US009670545B2

(12) United States Patent
McKernan et al.

(10) Patent No.: US 9,670,545 B2
(45) Date of Patent: Jun. 6, 2017

(54) METHODS AND KITS FOR TREATING AND CLASSIFYING INDIVIDUALS AT RISK OF OR SUFFERING FROM TRAP1 CHANGE-OF-FUNCTION

(71) Applicant: Courtagen Life Sciences, Inc., Woburn, MA (US)

(72) Inventors: Kevin McKernan, Woburn, MA (US); Richard Boles, Los Angeles, CA (US)

(73) Assignee: Coutagen Life Sciences, Inc., Woburn, MA (US)

( * ) Notice: Subject to any disclaimer, the term of this patent is extended or adjusted under 35 U.S.C. 154(b) by 0 days.

(21) Appl. No.: 14/895,557

(22) PCT Filed: Jun. 11, 2014

(86) PCT No.: PCT/US2014/041969
§ 371 (c)(1),
(2) Date: Dec. 3, 2015

(87) PCT Pub. No.: WO2014/201155
PCT Pub. Date: Dec. 18, 2014

(65) Prior Publication Data
US 2016/0186264 A1 Jun. 30, 2016

Related U.S. Application Data

(60) Provisional application No. 61/833,596, filed on Jun. 11, 2013.

(51) Int. Cl.
*A61K 31/00* (2006.01)
*C12Q 1/68* (2006.01)

(52) U.S. Cl.
CPC ..... *C12Q 1/6883* (2013.01); *C12Q 2600/106* (2013.01); *C12Q 2600/156* (2013.01)

(58) Field of Classification Search
CPC .................................................. A61K 31/00
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,863,849 A | 9/1989 | Melamede | |
| 4,889,818 A | 12/1989 | Gelfand et al. | |
| 5,302,509 A | 4/1994 | Cheeseman | |
| 5,547,835 A | 8/1996 | Koster | |
| 5,571,676 A | 11/1996 | Shuber | |
| 5,580,732 A | 12/1996 | Grossman et al. | |
| 5,605,798 A | 2/1997 | Koster | |
| 5,679,524 A | 10/1997 | Nikiforov et al. | |
| 5,740,341 A | 4/1998 | Oota et al. | |
| 5,945,283 A | 8/1999 | Kwok et al. | |
| 6,306,597 B1 | 10/2001 | MacEvicz | |
| 2013/0316911 A1 | 11/2013 | Scherer | |

FOREIGN PATENT DOCUMENTS

| | | |
|---|---|---|
| WO | WO-90/09455 A1 | 8/1990 |
| WO | WO-91/02087 A1 | 2/1991 |
| WO | WO-91/06678 A1 | 5/1991 |
| WO | WO-92/15712 A1 | 9/1992 |
| WO | WO-93/21340 A1 | 10/1993 |
| WO | WO-94/16101 A2 | 7/1994 |
| WO | WO-94/21822 A1 | 9/1994 |
| WO | WO-95/17676 A1 | 6/1995 |
| WO | WO-2005/003766 A2 | 1/2005 |
| WO | WO-2013/054200 A3 | 4/2013 |

OTHER PUBLICATIONS

Butler, E. et al., The Mitochondrial Chaperone Protein TRAP1 Mitigates α-Synuclein Toxicity, PLoS Genetics, 8(2):1-15 (2012).
Parikh, S. et al., A Modern Approach to the Treatment of Mitochondrial Disease, Curr Treat Options Neurol, 11(6):414-430 (2009).
Sheu, S. et al., Targeting antioxidants to mitochondria: A new therapeutic direction, Biochimica et Biophysica Acta, 1762:256-265 (2006).
Bhat, S. and Nagineni, C., alpha B subunit of lens-specific protein alpha-crystallin is present in other ocular and non-ocular tissues, Biochemical and Biophysical Research Communications, 158(1):319-325 (1989).
Canard, B. and Sarfati, R., DNA polymerase fluorescent substrates with reversible 3'-tags, Gene, 148(1):1-6 (1994).
Cechetto, J. and Gupta, R., Immunoelectron microscopy provides evidence that tumor necrosis factor receptor-associated protein 1 (TRAP-1) is a mitochondrial protein which also localizes at specific extramitochondrial sites, Experimental Cell Research, 260(1):30-39 (2000).
Cohen, A. et al., Emerging technologies for sequencing antisense oligonucleotides: capillary electrophoresis and mass spectrometry, Advances in Chromatography, 36:127-162 (1996).
Felts, S. et al., The hsp90-related protein TRAP1 is a mitochondrial protein with distinct functional properties, Jouranal of Biological Chemistry, 275(5):3305-3312 (2000).
Griffin, H. and Griffin, A., DNA sequencing. Recent innovations and future trends, Applied Biochemistry and Biotechnology, 38(1-2):147-159 (1993).
Hua, G. et al., Heat shock protein 75 (TRAP1) antagonizes reactive oxygen species generation and protects cells from granzyme M-mediated apoptosis, Journal of Biological Chemistry, 282(28):20553-20560 2007).
Im, C. et al., Iron chelation study in a normal human hepatocyte cell line suggests that tumor necrosis factor receptor-associated protein 1 (TRAP1) regulates production of reactive oxygen species, Journal of Cellular Biochemistry, 100(2):474-486 (2007).
International Search Report for PCT/US2014/041969, 4 pages (Oct. 29, 2014).

(Continued)

*Primary Examiner* — Rosanna Kosson
(74) *Attorney, Agent, or Firm* — Choate, Hall & Stewart LLP

(57) ABSTRACT

The present disclosure provides methods and kits for treating and classifying individuals at risk of or suffering from a neurological and/or mitochondrial dysfunction or disorder. In general, the individuals are treated and/or classified based on the presence of a change-of-function mutation in nuclear DNA that encodes TNF receptor-associated protein 1 (TRAP1). Treatment involves the administration of a therapeutically effective amount of an antioxidant.

15 Claims, 6 Drawing Sheets

(56) References Cited

OTHER PUBLICATIONS

Lander, E. et al., Initial sequencing and analysis of the human genome, Nature, 409:860-921 (2001).
Liu, D. et al., Tumor necrosis factor receptor-associated protein 1(TRAP1) regulates genes involved in cell cycle and metastases, Cancer Letters, 296(2):194-205 (2010).
Marzec, M. et al., GRP94: An HSP90-like protein specialized for protein folding and quality control in the endoplasmic reticulum, Biochimica et Biophysica Acta, 1823(3):774-787 (2012).
Matassa, D. et al., New insights into TRAP1 pathway, American Journal of Cancer Research, 2:235-248 (2012).
Maxam, A. and Gilbert, W., A new method for sequencing DNA, Proceedings of the National Academy of Sciences USA, 74(2):560-564 (1977).
Metzker, M. et al., Termination of DNA synthesis by novel 3'-modified-deoxyribonucleoside 5'-triphosphates, Nucleic Acids Research, 22(20):4259-4267 (1994).
Montesano, G. et al., Tumor necrosis factor-associated protein 1 (TRAP-1) protects cells from oxidative stress and apoptosis, Stress, 10(4):342-350 (2007).
Owen, B. et al., Regulation of heat shock protein 90 (HSP90) ATPase activity by sequences in the carboxyl terminus, The Journal of Biological Chemistry, 277:7086-7091 (2001).
Ozelius, L. et al., The early-onset torsion dystonia gene (DYT1) encodes an ATP-binding protein, Nature Genetics, 17(1):40-48 (1997).
Saisawat, P. et al., Whole-exome resequencing reveals recessive mutations in TRAP1 in individuals with CAKUT and VACTERL association, Kidney International, 85:1310-1317 (2013).
Sanger, F. et al., DNA sequencing with chain-terminating inhibitors, Proceedings of the National Academy of Sciences USA, 74(12):5463-5467 (1977).
Valente, E. et al., The role of DYT1 in primary torsion dystonia in Europe, Brain, 121( Pt 12):2335-2339 (1998).
Venter, J. et al., The sequence of the human genome, Science, 291(5507):1304-1351 (2001).
Written Opinion for PCT/US2014/041969, 12 pages (Oct. 29, 2014).
Zhu, S. and Tytgat, J., Evolutionary epitopes of Hsp90 and p23: implications for their interaction, The FASEB Journal, 18:940-947 (2004).

SEQUENCE LISTING

<160> NUMBER OF SEQ ID NOS: 2

<210> SEQ ID NO 1
<211> LENGTH: 704
<212> TYPE: PRT
<213> ORGANISM: Homo sapiens

<400> SEQUENCE: 1

Met Ala Arg Glu Leu Arg Ala Leu Leu Leu Trp Gly Arg Arg Leu Arg
1               5                   10                  15

Pro Leu Leu Arg Ala Pro Ala Leu Ala Ala Val Pro Gly Gly Lys Pro
            20                  25                  30

Ile Leu Cys Pro Arg Arg Thr Thr Ala Gln Leu Gly Pro Arg Arg Asn
        35                  40                  45

Pro Ala Trp Ser Leu Gln Ala Gly Arg Leu Phe Ser Thr Gln Thr Ala
    50                  55                  60

Glu Asp Lys Glu Pro Leu His Ser Ile Ile Ser Ser Thr Glu Ser
65                  70                  75                  80

Val Gln Gly Ser Thr Ser Lys His Glu Phe Gln Ala Glu Thr Lys Lys
                85                  90                  95

-continued

```
Leu Leu Asp Ile Val Ala Arg Ser Leu Tyr Ser Glu Lys Glu Val Phe
            100                 105                 110
Ile Arg Glu Leu Ile Ser Asn Ala Ser Asp Ala Leu Glu Lys Leu Arg
        115                 120                 125
His Lys Leu Val Ser Asp Gly Gln Ala Leu Pro Glu Met Glu Ile His
    130                 135                 140
Leu Gln Thr Asn Ala Glu Lys Gly Thr Ile Thr Ile Gln Asp Thr Gly
145                 150                 155                 160
Ile Gly Met Thr Gln Glu Glu Leu Val Ser Asn Leu Gly Thr Ile Ala
                165                 170                 175
Arg Ser Gly Ser Lys Ala Phe Leu Asp Ala Leu Gln Asn Gln Ala Glu
            180                 185                 190
Ala Ser Ser Lys Ile Ile Gly Gln Phe Gly Val Gly Phe Tyr Ser Ala
        195                 200                 205
Phe Met Val Ala Asp Arg Val Glu Val Tyr Ser Arg Ser Ala Ala Pro
    210                 215                 220
Gly Ser Leu Gly Tyr Gln Trp Leu Ser Asp Gly Ser Gly Val Phe Glu
225                 230                 235                 240
Ile Ala Glu Ala Ser Gly Val Arg Thr Gly Thr Lys Ile Ile His
                245                 250                 255
Leu Lys Ser Asp Cys Lys Glu Phe Ser Ser Glu Ala Arg Val Arg Asp
            260                 265                 270
Val Val Thr Lys Tyr Ser Asn Phe Val Ser Phe Pro Leu Tyr Leu Asn
        275                 280                 285
Gly Arg Arg Met Asn Thr Leu Gln Ala Ile Trp Met Met Asp Pro Lys
    290                 295                 300
Asp Val Arg Glu Trp Gln His Glu Glu Phe Tyr Arg Tyr Val Ala Gln
305                 310                 315                 320
Ala His Asp Lys Pro Arg Tyr Thr Leu His Tyr Lys Thr Asp Ala Pro
                325                 330                 335
Leu Asn Ile Arg Ser Ile Phe Tyr Val Pro Asp Met Lys Pro Ser Met
            340                 345                 350
Phe Asp Val Ser Arg Glu Leu Gly Ser Ser Val Ala Leu Tyr Ser Arg
        355                 360                 365
Lys Val Leu Ile Gln Thr Lys Ala Thr Asp Ile Leu Pro Lys Trp Leu
    370                 375                 380
Arg Phe Ile Arg Gly Val Val Asp Ser Glu Asp Ile Pro Leu Asn Leu
385                 390                 395                 400
Ser Arg Glu Leu Leu Gln Glu Ser Ala Leu Ile Arg Lys Leu Arg Asp
                405                 410                 415
Val Leu Gln Gln Arg Leu Ile Lys Phe Phe Ile Asp Gln Ser Lys Lys
            420                 425                 430
Asp Ala Glu Lys Tyr Ala Lys Phe Phe Glu Asp Tyr Gly Leu Phe Met
        435                 440                 445
Arg Glu Gly Ile Val Thr Ala Thr Glu Gln Glu Val Lys Glu Asp Ile
    450                 455                 460
Ala Lys Leu Leu Arg Tyr Glu Ser Ser Ala Leu Pro Ser Gly Gln Leu
465                 470                 475                 480
Thr Ser Leu Ser Glu Tyr Ala Ser Arg Met Arg Ala Gly Thr Arg Asn
                485                 490                 495
Ile Tyr Tyr Leu Cys Ala Pro Asn Arg His Leu Ala Glu His Ser Pro
            500                 505                 510
Tyr Tyr Glu Ala Met Lys Lys Lys Asp Thr Glu Val Leu Phe Cys Phe
```

```
                515                 520                 525
Glu Gln Phe Asp Glu Leu Thr Leu Leu His Leu Arg Glu Phe Asp Lys
        530                 535                 540

Lys Lys Leu Ile Ser Val Glu Thr Asp Ile Val Val Asp His Tyr Lys
545                 550                 555                 560

Glu Glu Lys Phe Glu Asp Arg Ser Pro Ala Ala Glu Cys Leu Ser Glu
                565                 570                 575

Lys Glu Thr Glu Glu Leu Met Ala Trp Met Arg Asn Val Leu Gly Ser
            580                 585                 590

Arg Val Thr Asn Val Lys Val Thr Leu Arg Leu Asp Thr His Pro Ala
        595                 600                 605

Met Val Thr Val Leu Glu Met Gly Ala Ala Arg His Phe Leu Arg Met
    610                 615                 620

Gln Gln Leu Ala Lys Thr Gln Glu Glu Arg Ala Gln Leu Leu Gln Pro
625                 630                 635                 640

Thr Leu Glu Ile Asn Pro Arg His Ala Leu Ile Lys Lys Leu Asn Gln
                645                 650                 655

Leu Arg Ala Ser Glu Pro Gly Leu Ala Gln Leu Leu Val Asp Gln Ile
            660                 665                 670

Tyr Glu Asn Ala Met Ile Ala Ala Gly Leu Val Asp Asp Pro Arg Ala
        675                 680                 685

Met Val Gly Arg Leu Asn Glu Leu Leu Val Lys Ala Leu Glu Arg His
    690                 695                 700

<210> SEQ ID NO 2
<211> LENGTH: 2310
<212> TYPE: DNA
<213> ORGANISM: Homo sapiens

<400> SEQUENCE: 2
gaggaagccc cgccccgcgc agcccgtcc  cgccccttcc catcgtgtac ggtcccgcgt      60
ggctgcgcgc ggcgctctgg gagtacgaca tggcgcgcga gctgcgggcg ctgctgctgt     120
ggggccgccg cctgcggcct ttgctgcggg cgccggcgct ggcggccgtg ccggaggaa      180 aaccaattct gtgtcctcgg aggaccacag cccagttggg ccccaggcga aacccagcct    240
ggagcttgca ggcaggacga ctgttcagca cgcagaccgc cgaggacaag gaggaacccc    300
tgcactcgat tatcagcagc acagagagcg tgcagggttc cacttccaaa catgagttcc    360
aggccgagac aaagaagctt ttggacattg ttgcccggtc cctgtactca gaaaagagg     420 tgtttatacg ggagctgatc tccaatgcca gcgatgcctt ggaaaaactg cgtcacaaac    480
tggtgtctga cggccaagca ctgccagaaa tggagattca cttgcagacc aatgccgaga    540
aaggcaccat caccatccag gatactggta tcgggatgac acaggaagag ctggtgtcca    600
acctggggac gattgccaga tcggggtcaa aggccttcct ggatgctctg cagaaccagg    660
ctgaggccag cagcaagatc atcggccagt tggagtggg  tttctactca gctttcatgg    720
tggctgacag agtggaggtc tattcccgct cggcagcccc ggggagcctg ggttaccagt    780
ggctttcaga tggttctgga gtgttttgaaa tcgccgaagc ttcgggagtt agaaccggga   840
caaaaatcat catccacctg aaatccgact gcaaggagtt ttccagcgag gcccgggtgc    900
gagatgtggt aacgaagtac agcaacttcg tcagcttccc cttgtacttg aatggaaggc    960
ggatgaacac cttgcaggcc atctggatga tggaccccaa ggatgtccgt gagtggcaac   1020
atgaggagtt ctaccgctac gtcgcgcagg ctcacgacaa gccccgctac accctgcact   1080
```

```
ataagacgga cgcaccgctc aacatccgca gcatcttcta cgtgcccgac atgaaaccgt    1140
ccatgtttga tgtgagccgg gagctgggct ccagcgttgc actgtacagc cgcaaagtcc    1200
tcatccagac caaggccacg gacatcctgc ccaagtggct gcgcttcatc cgaggtgtgg    1260
tggacagtga ggacattccc ctgaacctca gccgggagct gctgcaggag agcgcactca    1320
tcaggaaact ccgggacgtt ttacagcaga ggctgatcaa attcttcatt gaccagagta    1380
aaaaagatgc tgagaagtat gcaaagtttt ttgaagatta cggcctgttc atgcgggagg    1440
gcattgtgac cgccaccgag caggaggtca aggaggacat agcaaagctg ctgcgctacg    1500
agtcctcggc gctgccctcc gggcagctaa ccagcctctc agaatacgcc agccgcatgc    1560
gggccggcac ccgcaacatc tactacctgt gcgcccccaa ccgtcacctg gcagagcact    1620
caccctacta tgaggccatg aagaagaaag acacagaggt tctcttctgc tttgagcagt    1680
ttgatgagct caccctgctg caccttcgtg agtttgacaa gaagaagctg atctctgtgg    1740
agacggacat agtcgtggat cactacaagg aggagaagtt tgaggacagg tccccagccg    1800
ccgagtgcct atcagagaag gagacggagg agctcatggc ctggatgaga aatgtgctgg    1860
ggtcgcgtgt caccaacgtg aaggtgaccc tccgactgga cacccaccct gccatggtca    1920
ccgtgctgga gatgggggct gcccgccact tcctgcgcat gcagcagctg gccaagaccc    1980
aggaggagcg cgcacagctc ctgcagccca cgctggagat caaccccagg cacgcgctca    2040
tcaagaagct gaatcagctg cgcgcaagcg agcctggcct ggctcagctg ctggtggatc    2100
agatatacga gaacgccatg attgctgctg gacttgttga cgaccctagg gccatggtgg    2160
gccgcttgaa tgagctgctt gtcaaggccc tggagcgaca ctgacagcca gggggccaga    2220
aggactgaca ccacagatga cagccccacc tccttgagct ttatttacct aaatttaaag    2280
gtatttctta acccgaaaaa aaaaaaaaa                                      2310
```

METHODS AND KITS FOR TREATING AND CLASSIFYING INDIVIDUALS AT RISK OF OR SUFFERING FROM TRAP1 CHANGE-OF-FUNCTION

CROSS-REFERENCES TO RELATED APPLICATIONS

This application claims priority from U.S. provisional patent application Ser. No. 61/833,596, filed Jun. 11, 2013, the disclosures of which are hereby incorporated in their entirety.

SEQUENCE LISTING

The instant application contains a Sequence Listing which has been submitted electronically in ASCII format and is hereby incorporated by reference in its entirety. The ASCII copy, created on Mar. 14, 2016, is named 2010807_0018_SequenceListing.TXT and is 9.33 bytes in size.

BACKGROUND

Neurological dysfunctions and disorders continue to be a major health threat in the population. Neurological dysfunctions and disorders occur due to dysfunction of the neurons in the central nervous system as well as the peripheral nervous system.

One frequent contributing factor of neurological dysfunctions and disorders is mitochondrial disease. Some mitochondrial diseases are due to mutations or deletions in the mitochondrial genome. Mitochondria divide and proliferate with a faster turnover rate than their host cells, and their replication is under control of the nuclear genome. If a threshold proportion of mitochondria in a cell is defective, and if a threshold proportion of such cells within a tissue have defective mitochondria, symptoms of tissue or organ dysfunction can result. Practically any tissue can be affected, and a large variety of symptoms may be present, depending on the extent to which different tissues are involved.

SUMMARY

The present invention encompasses the recognition that inhibition of oxidative activity (e.g., oxidative stress) and/or radical oxygen species represents an effective therapy for neurological and/or mitochondrial dysfunctions or disorders, wherein the individual has one or more mutations that change the function (change-of-function mutations) of TNF receptor-associated protein 1 (TRAP1). In certain embodiments, a change-of-function mutation is in the ATPase domain. In certain embodiments, a change-of-function mutation is in the C-terminal HSP90-like domain. In certain embodiments, a change-of-function mutations is a gain-of-function mutation or a loss-of-function mutation. In certain embodiments, a mutation may be a specific TRAP1 mutation, for example I253V or any other mutation disclosed herein.

In one aspect, the present invention relates to methods and kits for treating and classifying individuals at risk of or suffering from a neurological and/or mitochondrial dysfunction or disorder, and in particular, those neurological and/or mitochondrial dysfunctions or disorders associated with change of function mutations in TRAP1, referred to hereafter as "disorders associated with TRAP1 change-of-function". In some embodiments disorders associated with TRAP1 change-of function are treated with an antioxidant. In certain embodiments, a change-of-function mutations is a gain-of-function mutation or a loss-of-function mutation. In certain embodiments, a mutation may be a specific TRAP1 mutation, for example I253V or any other mutation disclosed herein.

In certain embodiments, the present invention provides methods of treating an individual at risk of or suffering from a disorder associated with TRAP1 change-of function, the method comprising administering to the individual a therapeutically effective amount of an antioxidant, wherein nuclear DNA of the individual that encodes TRAP1 includes a change-of-function mutation. In certain embodiments, a change-of-function mutations is a gain-of-function mutation or a loss-of-function mutation. In certain embodiments, a mutation may be a specific TRAP1 mutation, for example I253V or any other mutation disclosed herein.

In certain embodiments, the present invention provides methods of treating an individual at risk of or suffering from a disorder associated with TRAP1 change-of function, the method comprising administering to the individual a therapeutically effective amount of an antioxidant, wherein, prior to administration, the individual has been determined to possess a change-of-function mutation in nuclear DNA that encodes TRAP1. In certain embodiments, a change-of-function mutations is a gain-of-function mutation or a loss-of-function mutation. In certain embodiments, a mutation may be a specific TRAP1 mutation, for example I253V or any other mutation disclosed herein.

In certain embodiments, the present invention provides methods of treating an individual at risk of or suffering from a disorder associated with TRAP1 change-of function, the method comprising determining that the individual possesses a change-of-function mutation in nuclear DNA that encodes TRAP1 and administering to the individual a therapeutically effective amount of an antioxidant. In certain embodiments, a change-of-function mutations is a gain-of-function mutation or a loss-of-function mutation. In certain embodiments, a mutation may be a specific TRAP1 mutation, for example I253V or any other mutation disclosed herein.

In certain embodiments, the present invention provides methods of aiding in the selection of a therapy for an individual at risk of or suffering from a disorder associated with TRAP1 change-of-function, the method comprising obtaining a sample of nuclear DNA from the individual, processing the sample to determine whether the individual possesses a change-of-function mutation in nuclear DNA that encodes TRAP1 and classifying the individual as one that could benefit from therapy with an antioxidant if the step of processing determines that the individual possesses a change-of-function mutation in nuclear DNA that encodes TRAP1. In some embodiments, processing comprises sequencing at least a portion of nuclear DNA that encodes TRAP1. In some embodiments, the methods further comprise administering to the individual a therapeutically effective amount of an antioxidant. In certain embodiments, a change-of-function mutations is a gain-of-function mutation or a loss-of-function mutation. In certain embodiments, a mutation may be a specific TRAP1 mutation, for example I253V or any other mutation disclosed herein.

In certain embodiments, the present invention provides methods of classifying an individual at risk of or suffering from a disorder associated with TRAP1 change-of-function, the method comprising obtaining a sample of nuclear DNA from the individual, processing the sample to determine whether the individual possesses a mutation in nuclear DNA that encodes TRAP1, and classifying the individual as one that does or does not possess a mutation in nuclear DNA that encodes TRAP1. In some embodiments, processing comprises sequencing at least a portion of nuclear DNA that encodes TRAP1. In some embodiments, the mutation is a change-of-function mutation. In some embodiments, the change-of-function mutation is in the ATPase domain. In some embodiments, the change-of-function mutation is in the C-terminal HSP90-like domain. In some embodiments, the methods further comprise providing the individual or a physician treating the individual with information regarding the mutation. In some embodiments, the information references a correlation between the mutation and the potential benefits of therapy with an antioxidant. In certain embodiments, a change-of-function mutations is a gain-of-function mutation or a loss-of-function mutation. In certain embodiments, a mutation may be a specific TRAP1 mutation, for example I253V or any other mutation disclosed herein.

In certain embodiments, the present invention provides kits for classifying an individual at risk of or suffering from a disorder associated with TRAP1 change-of-function, the kit comprising primers for amplifying a target region of nuclear DNA that encompasses part or all of the codon for amino acids 165, 192, 216, 253, 266, 340, 388, 444, 455, 457, 469, 535 and/or 685 of a TRAP1 gene product. In certain embodiments, the present disclosure provides kits for classifying an individual at risk of or suffering from a disorder associated with TRAP1 change-of-function, the kit comprising primers for amplifying a target region of nuclear DNA encompassing a region of the TRAP1 gene, wherein said region includes one or more sites of change-of-function mutations that are associated with a disorder associated with TRAP1 change-of-function. In certain embodiments, a change-of-function mutations is a gain-of-function mutation or a loss-of-function mutation. In certain embodiments, a mutation may be a specific TRAP1 mutation, for example I253V or any other mutation disclosed herein.

In some embodiments, according to the methods and kits described herein, the disorder associated with TRAP1 change-of-function is selected from the group consisting of abnormal autonomic activity, functional gastrointestinal disorders, chronic pain disorders, autistic spectrum disorders, psychiatric disorders, cognitive dysfunction, and combinations thereof. In some embodiments, the individual has suffered from episodic dementia/psychosis prior to administration. In some embodiments, the individual has suffered from intestinal pseudo-obstruction prior to administration. In some embodiments, the individual has suffered from an autistic spectrum disorder prior to administration. In some embodiments, the individual has suffered from intermittent encephalopathy prior to administration. In some embodiments, the individual has suffered from dementia prior to administration. In some embodiments, the individual has suffered from cognitive decline prior to administration. In some embodiments, the individual has suffered from migraines prior to administration. In some embodiments, the individual has suffered an adverse reaction to an anticholinergic medication prior to administration. In certain embodiments, a change-of-function mutations is a gain-of-function mutation or a loss-of-function mutation. In certain embodiments, a mutation may be a specific TRAP1 mutation, for example I253V or any other mutation disclosed herein.

In some embodiments, according to the methods and kits described herein, the individual suffers from a mitochondrial dysfunction. In some embodiments, the individual further possesses homoplasmic mitochondrial DNA variants. In some embodiments, the methods described herein further comprise sequencing mitochondrial DNA obtained from the individual. In some embodiments, the mitochondrial DNA of the individual has been sequenced without identifying heteroplasmic mitochondrial DNA variants.

In some embodiments, according to the methods and kits described herein, the change-of-function mutation causes reduced expression of a TRAP1 gene product. In some embodiments, the change-of-function mutation is in the regulatory sequence of the TRAP1 gene. In some embodiments, the change-of-function mutation is in the coding sequence of the TRAP1 gene. In some embodiments, the change-of-function mutation causes reduced activity of a TRAP1 gene product. In some embodiments, the change-of-function mutation is or comprises a mutation selected from the group consisting of 165Q>E, 192E>K, 216E>*, 253I>V, 266S>R, 340R>H, 388R>Q, 444Y>N, 455G>S, 457E>K, 469R>H, 535T>S, 685D>N, and combinations thereof.

In some embodiments, according to the methods and kits described herein, the change-of-function mutation causes increased expression of a TRAP1 gene product. In some embodiments, the change-of-function mutation is in the regulatory sequence of the TRAP1 gene. In some embodiments, the change-of-function mutation is in the coding sequence of the TRAP1 gene. In some embodiments, the change-of-function mutation causes increased activity of a TRAP1 gene product. In some embodiments, the change-of-function mutation is or comprises a mutation selected from the group consisting of 165Q>E, 192E>K, 216E>*, 253I>V, 266S>R, 340R>H, 388R>Q, 444Y>N, 455G>S, 457E>K, 469R>H, 535T>S, 685D>N, and combinations thereof.

In some embodiments, according to the methods and kits described herein, the antioxidant is selected from the group consisting of Vitamin C (e.g., ascorbic acid), Vitamin A (e.g., retinol, retinal, retinoic acid, beta-carotene, etc.), Vitamin E (e.g., tocopherols, tocotrienols, etc.), polyphenols, N-acetyl cysteine, Coenzyme $Q_{10}$, alpha-tocopherol, alpha-tocotrienol (EPI-743), Idebenone, cannabidiol and pharmaceutically acceptable salts thereof.

The present invention also provides, among other things, a method of building a database for use in selecting a medication (e.g., an antioxidant) for a patient. The method includes receiving, in a computer system, a plurality of genotyped polymorphisms for TRAP1 (e.g., 165Q>E, 192E>K, 216E>*, 253I>V, 266S>R, 340R>H, 388R>Q, 444Y>N, 455G>S, 457E>K, 469R>H, 535T>S or 685D>N); receiving a plurality of medication profiles specified based on the polymorphisms; and storing the plurality of polymorphisms and the medication profiles such that each medication profile is associated with one of the genotypes. The at least one medication profile can identify a medication and the medication can be placed in one of multiple categories included in the medication profile. Such categories can be selected from the group consisting of: medications that are safe to use, medications that should be used with caution, medications that should be closely monitored when used, medications that should be avoided, and combinations thereof. The medication profile can identify a universe of possible medications for the patient's genotype.

In another aspect, the invention features a computer program product containing executable instructions that when executed cause a processor to perform operations. The operations can include: receive a plurality of genotyped polymorphisms for TRAP1; receive a plurality of medication profiles specified based on the genotypes; and store the genotypes and the medication profiles such that each medication profile is associated with one of the genotypes.

The invention also features a method of selecting a medication (e.g., antioxidant) for a patient. The method includes receiving, in a computer system, a patient's genotyped polymorphisms for TRAP1; identifying, in a database comprising a plurality of medication profiles associated with genotypes, a medication profile that is associated with the patient's genotype; and outputting the identified medication profile in response to receiving the patient's genotype. A user can enter the patient's genotype in the computer system or the patient's genotype can be received directly from equipment used in determining the patient's genotype.

The medication profile can include a ranking of several medications, e.g., based on specific co-factors (e.g., clinical symptoms). The method can include adjusting the ranking before outputting the identified medication profile (e.g., based on receiving a genotypic polymorphism carried by the patient or based on receiving a clinical response relating to the patient). The clinical response can be by a family member of the patient.

In yet another aspect, the invention features a computer program product containing executable instructions that when executed cause a processor to perform operations that include receive a patient's genotyped polymorphisms for TRAP1; identify, in a database including a plurality of medication profiles associated with genotypes, a medication profile that is associated with the patient's genotype; and output the identified medication profile in response to receiving the patient's genotype.

BRIEF DESCRIPTION OF THE DRAWING

The Figures described below, that together make up the Drawing, are for illustration purposes only, not for limitation.

DEFINITIONS

Figure 1:
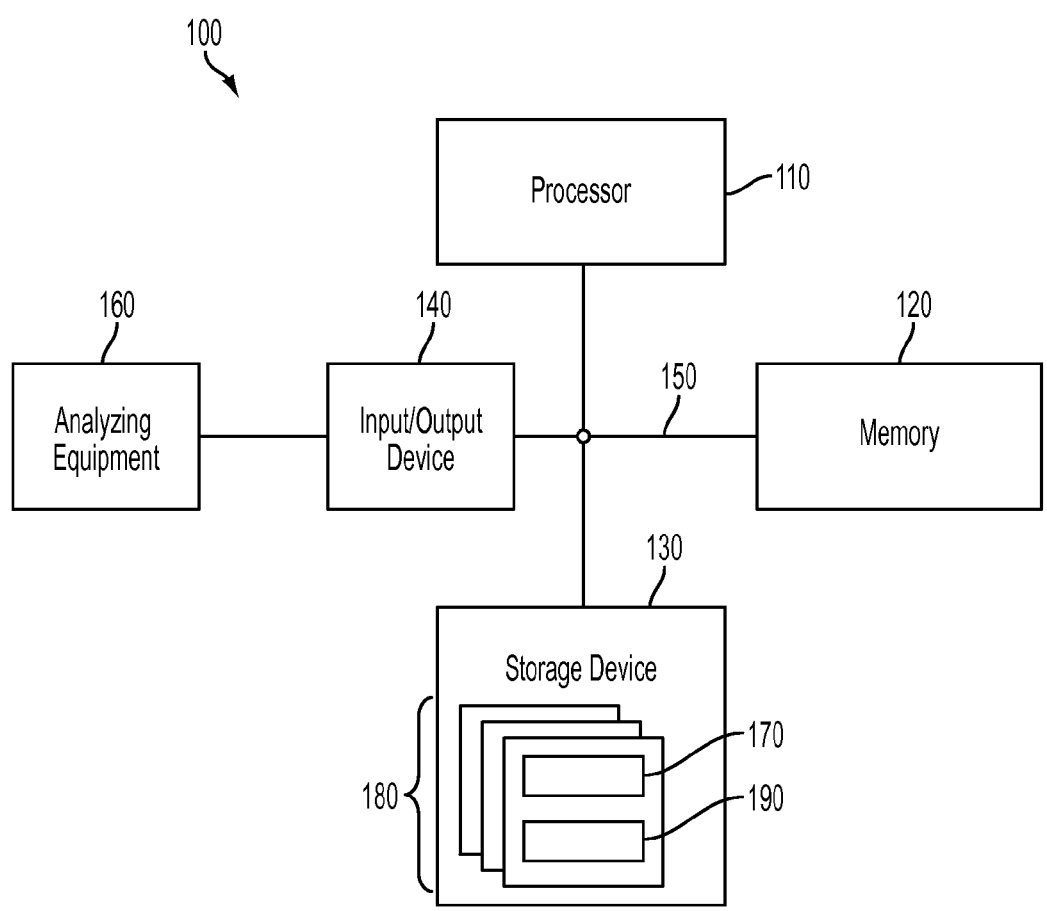
FIG. 1: depicts an exemplary block diagram of a computer system 100.

Antioxidant: As used herein, the term "antioxidant" refers to any natural or synthesized compounds or molecules that inhibit the oxidation of other compounds or molecules. In some embodiments, antioxidants are reducing agents. Examples of antioxidants include, but are not limited to Vitamin C (e.g., ascorbic acid), Vitamin A (e.g., retinol, retinal, retinoic acid, beta-carotene, etc.), Vitamin E (e.g., tocopherols, tocotrienols, etc.), polyphenols, N-acetyl cysteine, Coenzyme $Q_{10}$, alpha-tocopherol, alpha-tocotrienol (EPI-743), Idebenone and cannabidiol.

Associated With: The term "associated with" is used herein to describe an observed correlation between two items or events. For example, a change-of-function mutation in TRAP1 may be considered to be "associated with" a particular neurological dysfunction or disorder if its presence or level correlates with a presence or level of the dysfunction or disorder.

Coding sequence: As used herein, the term "coding sequence" refers to a sequence of a nucleic acid or its complement, or a part thereof, that can be transcribed and/or translated to produce the mRNA for and/or the polypeptide or a fragment thereof. Coding sequences include exons in genomic DNA or immature primary RNA transcripts, which are joined together by the cell's biochemical machinery to provide a mature mRNA.

Dosage form: As used herein, the terms "dosage form" and "unit dosage form" refer to a physically discrete unit of a therapeutic composition for administration to a subject to be treated. Each unit dosage form contains a predetermined quantity of active agent (for example, an antioxidant) calculated to produce a desired therapeutic effect when administered in accordance with a dosing regimen. It will be understood, however, that a total dosage of the active agent may be decided by an attending physician within the scope of sound medical judgment.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent (for example, an antioxidant) has a recommended dosing regimen, which may involve one or more doses.

Gene: The term "gene", as used herein, has its art understood meaning, and refers to a part of the genome specifying a macromolecular product, be it DNA for incorporation into a host genome, a functional RNA molecule or a protein, and may include regulatory sequences (e.g., promoters, enhancers, etc.) and/or intron sequences preceding (5' non-coding sequences Heteroplasmic mitochondrial DNA variants: As used herein, the term "heteroplasmic mitochondrial DNA variants" refers to a mutation in mitochondrial DNA that affects a proportion of the mitochondrial DNA, while the remaining mitochondrial DNA is wild-type. In some embodiments, 0, 1, 2, 3, 4, 5, 6, 7, 8, 9, 10% or more of the mitochondrial DNA possesses the mutation.

Homoplasmic mitochondrial DNA variants: As used herein, the term "homoplasmic mitochondrial DNA variants" refers to a mutation in mitochondrial DNA that affects substantially all of the mitochondrial DNA Change-of-function mutation: As used herein, the term "change-of-function mutation" refers to a mutation that is associated with a change of the normal activity of a gene or gene product. Change of activity can be due to an increase or decrease in transcription and/or processing of the RNA, an increase or decrease in translation, stability, transport, or activity of the gene product, or any combination thereof. In some embodiments, normal activity of a gene or gene product is changed from 0, 1, 2, 3, 4, 5, 6, 7, 8, 9, 10 up to 100%.

Loss-of-function mutation: As used herein, the term "loss-of-function mutation" refers to a mutation that is associated with a reduction or elimination of the normal activity of a gene or gene product. Loss of activity can be due to a decrease in transcription and/or processing of the RNA, a decrease in translation, stability, transport, or activity of the gene product, or any combination thereof. In some embodiments, normal activity of a gene or gene product is reduced from 0, 1, 2, 3, 4, 5, 6, 7, 8, 9, 10 up to 100%.

Gain-of-function mutation: As used herein, the term "gain-of-function mutation" refers to a mutation that is associated with an increase of the normal activity of a gene or gene product. Increase of activity can be due to an increase in transcription and/or processing of the RNA, an increase in translation, stability, transport, or activity of the gene product, or any combination thereof. In some embodiments, normal activity of a gene or gene product is increased from 0, 1, 2, 3, 4, 5, 6, 7, 8, 9, 10 up to 100%.

Mitochondrial DNA: As used herein, the term "mitochondrial DNA" refers to the part of the genome that is located in the mitochondria of a cell.

Mutation: As used herein, the term "mutation" refers to a change introduced into a parental sequence, including, but not limited to, substitutions, insertions, deletions (including truncations). The consequences of a mutation include, but are not limited to, the creation of a new character, property, function, phenotype or trait not found in the protein encoded by the parental sequence, or the increase or reduction/elimination of an existing character, property, function, phenotype or trait not found in the protein encoded by the parental sequence.

Nuclear DNA: As used herein, the term "nuclear DNA" refers to the part of the genome that is located in the nucleus of a cell.

Nucleic Acid: The terms "nucleic acid", "nucleic acid molecule", and "polynucleotide" each is used herein to refer to a polymers of nucleotide monomers or analogs thereof, such as deoxyribonucleic acid (DNA) and ribonucleic acid (RNA). Unless otherwise stated, the terms encompass nucleic acid-like structures with synthetic backbones, as well as amplification products. In some embodiments, nucleic acids involved in the present invention are linear nucleic acids.

Primer: The terms "primer", as used herein, typically refers to oligonucleotides that hybridize in a sequence specific manner to a complementary nucleic acid molecule (e.g., a nucleic acid molecule comprising a target sequence). In some embodiments, a primer will comprise a region of nucleotide sequence that hybridizes to at least about 8, e.g., at least about 10, at least about 15, or about 20 to about 40 consecutive nucleotides of a target nucleic acid (i.e., will hybridize to a contiguous sequence of the target nucleic acid). In general, a primer sequence is identified as being either "complementary" (i.e., complementary to the coding or sense strand (+)), or "reverse complementary" (i.e., complementary to the anti-sense strand (−)). In some embodiments, the term "primer" may refer to an oligonucleotide that acts as a point of initiation of a template-directed synthesis using methods such as PCR (polymerase chain reaction) under appropriate conditions (e.g., in the presence of four different nucleotide triphosphates and a polymerization agent, such as DNA polymerase in an appropriate buffer solution containing any necessary reagents and at suitable temperature(s)). Such a template directed synthesis is also called "primer extension". For example, a primer pair may be designed to amplify a region of DNA using PCR. Such a pair will include a "forward primer" and a "reverse primer" that hybridize to complementary strands of a DNA molecule and that delimit a region to be synthesized and/or amplified.

Reference: As will be understood from context, a reference sequence, sample, population, agent or individual is one that is sufficiently similar to a particular sequence, sample, population, agent or individual of interest to permit a relevant comparison (i.e., to be comparable). In some embodiments, information about a reference sample is obtained simultaneously with information about a particular sample. In some embodiments, information about a reference sample is historical. In some embodiments, information about a reference sample is stored for example in a computer-readable medium. In some embodiments, comparison of a particular sample of interest with a reference sample establishes identity with, similarity to, or difference of a particular sample of interest relative to a reference.

Regulatory Sequence: The term "regulatory sequence" is intended to include promoters, enhancers and other expression control elements (e.g., polyadenylation signals).

Risk: As will be understood from context, a "risk" of a disease, disorder or condition (e.g., a neurological dysfunction or disorder) comprises a likelihood that a particular individual will develop the disease, disorder, or condition. In some embodiments, risk is expressed as a percentage. In some embodiments, risk is from 0, 1, 2, 3, 4, 5, 6, 7, 8, 9, 10 up to 100%. In some embodiments risk is expressed as a risk relative to a risk associated with a reference sample or group of reference samples. In some embodiments, a reference sample or group of reference samples have a known risk of a disease, disorder, or condition (e.g., a mitochondrial and/or neurological dysfunction or disorder). In some embodiments a reference sample or group of reference samples are from individuals comparable to a particular individual. In some embodiments, relative risk is 0, 1, 2, 3, 4, 5, 6, 7, 8, 9, 10 or more.

Sample: As used herein, the term "sample" typically refers to a biological sample obtained or derived from a source of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids extracted from a sample or obtained by subjecting a primary sample to techniques such as amplification, isolation and/or purification of certain components, etc.

Suffering from: An individual who is "suffering from" a disease, disorder, and/or condition has been diagnosed with or displays one or more symptoms of the disease, disorder, and/or condition.

Therapeutically effective amount: As used herein, the term "therapeutically effective amount" refers to an amount of a therapeutic composition (e.g., an antioxidant which confers a therapeutic effect on a treated subject, at a reasonable benefit/risk ratio applicable to any medical treatment. A therapeutic effect may be objective (i.e., measurable by some test or marker) or subjective (i.e., subject gives an indication of or feels an effect). In particular, a "therapeutically effective amount" refers to an amount of a therapeutic composition effective to treat, ameliorate, or prevent a desired disease or condition, or to exhibit a detectable therapeutic or preventative effect, such as by ameliorating symptoms associated with a disease, preventing or delaying onset of a disease, and/or also lessening severity or frequency of symptoms of a disease. A therapeutically effective amount is commonly administered in a dosing regimen that may comprise multiple unit doses. A therapeutically effective amount (and/or an appropriate unit dose within an effective dosing regimen) may vary, for example, depending on route of administration, combination with other agents, etc.

Treatment: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

Wild type: As used herein, the term "wild-type" refers to a typical or common form existing in nature; in some embodiments it is the most common form.

DETAILED DESCRIPTION OF CERTAIN EMBODIMENTS

TNF Receptor-Associated Protein 1 (TRAP1)

Tumor necrosis factor receptor-associated protein 1 (TRAP1), also known as heat shock protein 75 (HSP75), is a member of the HSP90 family. Located at 16p13.3, TRAP1 contains 19 exons and 701 amino acids, with an N-terminal mitochondria-targeting sequence spanning positions 1-59, an ATPase domain at 108 to 260, and a C-terminal chaperone domain at 292-701 with significant homology to other HSP peptides in its family. The HSP90 proteins are highly-conserved molecular chaperones that play important roles in folding newly synthesized proteins, stabilizing and refolding denatured proteins, and inhibiting cellular death caused by reactive oxygen species (ROS) (Im C. M. et al. (2007) J Cell Biochem 100:474-86). While primarily a mitochondrial matrix protein, TRAP1 has also been identified in non-mitochondrial locations including pancreatic zymogen granules, insulin secretory granules, cardiac sarcomeres, and the nuclei of heart and pancreatic cells, suggesting broader functions (Cechetto J. D. & Gupta R. S. (2000) Experimental Cell Research 260:30-39). The role of TRAP1 as a protector against oxidative stress was one of its earliest recognized functions. Several groups have observed that overexpressing TRAP1 resulted in a reduction of oxidative damage and apoptosis in response to agents known to be toxic to mitochondria (deferoxamine and cisplatin, respectively), suggesting that TRAP1 plays a role in protecting mitochondria by reducing reactive oxygen species (ROS) levels (Im C. M. et al. (2007) J Cell Biochem 100:474-86; Montesano Gesualdi N. et al. (2007) Stress 10:342-50). Inversely, one group observed that silencing TRAP1 through RNA interference increases ROS accumulation (Hua G. et al. (2007) J Biol Chem 282:20553-20560).

TRAP1 has an ATPase domain, like other HSP90 proteins (Marzec M. et al. (2012) Biochim Biophys Acta 1823:774-87), which conceivably is involved in processing proteins in an energy-requiring manner. Defective chaperone function in TRAP1 proteins lacking proper ATPase ability, due to mutation in this domain, might process proteins in an inappropriate manner (e.g. mis-folding), and such a mutation (loss-of-function or gain-of-function) might result in dominant inheritance. This may explain dominant inheritance for I253V and other TRAP1 ATPase domain mutations, but lack of a discernible phenotype from mutation occurring in the same protein outside this domain (whereas inheritance might be recessive). Dominantly-inherited chaperonopathies have been described, including early-onset torsion (DYT1) (Valente E. M. (1998) Brain 121:2335-2339; Ozelius L. J. et al. (1997) Nat Genet 17:40-48) and myofibrillar myopathy (CRYAB) (Bhat S. P. and Nagineni C. N. (1989) Biochem Biophys Res Commun 158:319-25).

Expression of TRAP1 includes, but is not limited to, expression in skeletal muscle, liver, heat, brain, kidney, pancreas, lung and placenta. In some embodiments, TRAP1 is localized to the cytoplasm, nucleus and/or mitochondria. Although TRAP1 expression has been found in the cytoplasm and nucleus, the localization of this protein is largely limited to mitochondria.

TRAP1 contains three major domains: an N-terminal Mitochondria-Targeting Sequence (MTS) domain (amino acid residues 1-59 of SEQ ID NO: 1), an ATPase domain containing four ATP-binding sites (amino acid residues 108-260 of SEQ ID NO: 1) and a C-terminal HSP90-like domain (amino acid residues 292-701 of SEQ ID NO: 1). In some embodiments, TRAP1 undergoes post-translational modifications including, but not limited to acetylation (N6-acetyl-lysine at residues 87, 332, 382, 424, 466) and phosphorylation (phosphotyrosine 366, phosphoserine 401, phosphothreonine 494).

TRAP1 has been purified, characterized, cloned and sequenced from both mouse and human sources. The human TRAP1 mitochondrial isoform 1 precursor protein (NP_057376.2; SEQ ID NO: 1) contains 704 amino acid residues. Exemplary amino acid and nucleotide sequence from a full-length human TRAP1 polypeptide are shown below as SEQ ID NOs: 1 and 2. The NCBI consensus CDS (CCDS) identifier for TRAP1 is CCDS ID 10508.1.

TABLE 1

Exemplary TRAP1 sequences

| | |
|---|---|
| Human TRAP1 Protein Sequence mitchondrial isoform 1 precursor (NCBI Reference Sequence: NP_057376.2) | MARELRALLLWGRRLRPLLRAPALAAVPGGKPILCPRRTTAQLGP RRNPAWSLQAGRLFSTQTAEDKEEPLHSIISSTESVQGSTKHEF QAETKKLLDIVARSLYSEKEVFIRELISNASDALEKLRHKLVSDG QALPEMEIHLQTNAEKGTITIQDTGIGMTQEELVSNLGTIARSGS KAFLDALQNQAEASSKIIGQFGVGFYSAFMVADRVEVYSRSAAPG SLGYQWLSDGSGVFEIAEASGVRTGTKIIIHLKSDCKEFSSEARV RDVVTKYSNFVSFPLYLNGRRMNTLQAIWMMDPKDVREWQHEEFY |

TABLE 1-continued

Exemplary TRAP1 sequences

|  |  |
|---|---|
|  | RYVAQAHDKPRYTLHYKTDAPLNIRSIFYVPDMKPSMFDVSRELG<br>SSVALYSRKVLIQTKATDILPKWLRFIRGVVDSEDIPLNLSRELL<br>QESALIRKLRDVLQQRLIKFFIDQSKKDAEKYAKFFEDYGLFMRE<br>GIVTATEQEVKEDIAKLLRYESSALPSGQLTSLSEYASRMRAGTR<br>NIYYLCAPNRHLAEHSPYYEAMKKKDTEVLFCFEQFDELTLLHLR<br>EFDKKKLISVETDIVVDHYKEEKFEDRSPAAECLSEKETEELMAW<br>MRNVLGSRVTNVKVTLRLDTHPAMVTVLEMGAARHFLRMQQLAKT<br>QEERAQLLQPTLEINPRHALIKKLNQLRASEPGLAQLLVDQIYEN<br>AMIAAGLVDDPRAMVGRLNELLVKALERH (SEQ ID NO: 1) |
| Human TRAP1<br>mRNA Sequence<br>mitchondrial<br>isoform 1 precursor<br>(NCBI Reference<br>Sequence:<br>NM_016292.2) | GAGGAAGCCCCGCCCCGCGCAGCCCCGTCCCGCCCCTTCCCATCG<br>TGTACGGTCCCGCGTGGCTGCGCGCGGCGCTCTGGGAGTACGACA<br>TGGCGCGCGAGCTGCGGGCGCTGCTGCTGTGGGGCCGCCGCCTGC<br>GGCCTTTGCTGCGGGCGCCGGCGCTGGCGGCCGTGCCGGGAGGAA<br>AACCAATTCTGTGTCCTCGGAGGACCACAGCCCAGTTGGGCCCCA<br>GGCGAAACCCAGCCTGGAGCTTGCAGGCAGGACGACTGTTCAGCA<br>CGCAGACCGCCGAGGACAAGGAGGAACCCCTGCACTCGATTATCA<br>GCAGCACAGAGAGCGTGCAGGGTTCCACTTCCAAACATGAGTTCC<br>AGGCCGAGACAAAGAAGCTTTTGGACATTGTTGCCCGGTCCCTGT<br>ACTCAGAAAAAGAGGTGTTTATACGGGAGCTGATCTCCAATGCCA<br>GCGATGCCTTGGAAAAACTGCGTCACAAACTGGTGTCTGACGGCC<br>AAGCACTGCCAGAAATGGAGATTCACTTGCAGACCAATGCCGAGA<br>AAGGCACCATCACCATCCAGGATACTGGTATCGGGATGACACAGG<br>AAGAGCTGGTGTCCAACCTGGGGACGATTGCCAGATCGGGGTCAA<br>AGGCCTTCCTGGATGCTCTGCAGAACCAGGCTGAGGCCAGCAGCA<br>AGATCATCGGCCAGTTTGGAGTGGGTTTCTACTCAGCTTTCATGG<br>TGGCTGACAGAGTGGAGGTCTATTCCCGCTCGGCAGCCCCGGGGA<br>GCCTGGGTTACCAGTGGCTTTCAGATGGTTCTGGAGTGTTTGAAA<br>TCGCCGAAGCTTCGGGAGTTAGAACCGGGACAAAAATCATCATCC<br>ACCTGAAATCCGACTGCAAGGAGTTTTCCAGCGAGGCCCGGGTGC<br>GAGATGTGGTAACGAAGTACAGCAACTTCGTCAGCTTCCCCTTGT<br>ACTTGAATGGAAGGCGGATGAACACCTTGCAGGCCATCTGGATGA<br>TGGACCCCAAGGATGTCCGTGAGTGGCAACATGAGGAGTTCTACC<br>GCTACGTCGCGCAGGCTCACGACAAGCCCCGCTACACCCTGCACT<br>ATAAGACGGACGCACCGCTCAACATCCGCAGCATCTTCTACGTGC<br>CCGACATGAAACCGTCCATGTTTGATGTGAGCCGGGAGCTGGGCT<br>CCAGCGTTGCACTGTACAGCCGCAAAGTCCTCATCCAGACCAAGG<br>CCACGGACATCCTGCCCAAGTGGCTGCGCTTCATCCGAGGTGTGG<br>TGGACAGTGAGGACATTCCCCTGAACCTCAGCCGGGAGCTGCTGC<br>AGGAGAGCGCACTCATCAGGAAACTCCGGGACGTTTTACAGCAGA<br>GGCTGATCAAATTCTTCATTGACCAGAGTAAAAAAGATGCTGAGA<br>AGTATGCAAAGTTTTTTGAAGATTACGGCCTGTTCATGCGGGAGG<br>GCATTGTGACCGCCACCGAGCAGGAGGTCAAGGAGGACATAGCAA<br>AGCTGCTGCGCTACGAGTCCTCGGCGCTGCCCTCCGGGCAGCTAA<br>CCAGCCTCTCAGAATACGCCAGCCGCATGCGGGCCGGCACCCGCA<br>ACATCTACTACCTGTGCGCCCCCAACCGTCACCTGGCAGAGCACT<br>CACCCTACTATGAGGCCATGAAGAAGAAAGACACAGAGGTTCTCT<br>TCTGCTTTGAGCAGTTTGATGAGCTCACCCTGCTGCACCTTCGTG<br>AGTTTGACAAGAAGAAGCTGATCTCTGTGGAGACGGACATAGTCG<br>TGGATCACTACAAGGAGGAGAAGTTTGAGGACAGGTCCCCAGCCG<br>CCGAGTGCCTATCAGAGAAGGAGACGGAGGAGCTCATGGCCTGGA<br>TGAGAAATGTGCTGGGGTCGCGTGTCACCAACGTGAAGGTGACCC<br>TCCGACTGGACACCCACCCTGCCATGGTCACCGTGCTGGAGATGG<br>GGGCTGCCCGCCACTTCCTGCGCATGCAGCAGCTGGCCAAGACCC<br>AGGAGGAGCGCGCACAGCTCCTGCAGCCCACGCTGGAGATCAACC<br>CCAGGCACGCGCTCATCAAGAAGCTGAATCAGCTGCGCGCAAGCG<br>AGCCTGGCCTGGCTCAGCTGCTGGTGGATCAGATATACGAGAACG<br>CCATGATTGCTGCTGGACTTGTTGACGACCCTAGGGCCATGGTGG<br>GCCGCTTGAATGAGCTGCTTGTCAAGGCCCTGGAGCGACACTGAC<br>AGCCAGGGGGCCAGAAGGACTGACACCCACAGATGACAGCCCCACC<br>TCCTTGAGCTTTATTTACCTAAATTTAAAGGTATTTCTTAACCCG<br>AAAAAAAAAAAAAAA (SEQ ID NO: 2) |

Changed TRAP1 Function and Neurological Dysfunction or Disorders

The present invention encompasses the recognition that changed TRAP1 function is associated with a risk or susceptibility to a neurological dysfunction or disorder. In some embodiments, a neurological dysfunction or disorder is any dysfunction or disorder that result in impairment of neuronal mediated functions and includes disorders of the central nervous system (e.g., the brain, spinal cord) as well as the peripheral nervous system. In some embodiments, a neurological dysfunction or disorder comprises abnormal autonomic activity. In some embodiments, a neurological dysfunction or disorder comprises functional gastrointestinal disorders (e.g., GI dysmotility, gastroesophageal reflux disease (i.e., GERD), small bowel disease, large bowel disease, irritable bowel syndrome, constipation, cyclic vomiting syndrome, etc.). In some embodiments, a neurological dysfunction or disorder comprises chronic pain disorders (e.g., migraine, abdominal pain, myalgia, etc.). In some embodiments, a neurological dysfunction or disorder comprises chronic fatigue disorders. In some embodiments, a neurological dysfunction or disorder comprises autistic spectrum disorders. In some embodiments, a neurological dysfunction or disorder comprises psychiatric disorders. In some embodiments, a neurological dysfunction or disorder comprises cognitive dysfunction and/or decline. In some embodiments, a neurological dysfunction or disorder comprises episodic encephalopathy. In some embodiments, a neurological dysfunction or disorder comprises episodic dementia/psychosis.

In some embodiments, a risk of a neurological dysfunction or disorder comprises a risk from 1, 2, 3, 4, 5, 6, 7, 8, 9, 10, 15, 20, 25, 30, 35, 40, 45, 50, 55, 60, 65, 70, 75, 80, 85, 90, 95, 100, 1000% or more relative to a reference. In some embodiments, a reference comprises an average occurrence of a neurological dysfunction or disorder in a population. In some embodiments, a reference comprises a statistical occurrence of a neurological dysfunction or disorder deemed to be acceptable or unavoidable in a population by medical professionals.

Changed TRAP1 Function and Mitochondrial Dysfunction or Disorders

The present invention encompasses the recognition that changed TRAP1 function is associated with a risk or susceptibility to a mitochondrial dysfunction or disorder. As used herein, the term "mitochondrial diseases or disorders" refers to a complex variety of symptoms. In some embodiments, a mitochondrial dysfunction or disorder is any dysfunction or disorder that affects the mitochondria, the organelles that generate energy for the cell. In some embodiments, a mitochondrial dysfunction or disorder includes, but is not limited to muscle weakness, muscle cramps, seizures, food reflux, learning disabilities, deafness, short stature, paralysis of eye muscles, diabetes, cardiac problems and stroke—like episodes. The symptoms can range in severity from life-threatening to almost unnoticeable, sometimes taking both extremes in members of the same family. Because some people have specific subsets of these symptoms, clinical researchers have grouped those that occur together into "syndromes," producing a bewildering array of descriptive acronyms such as MELAS (mitochondrial encephalomyopathy with lactic acidosis and stroke-like episodes) or MERFF (myoclonus epilepsy with ragged red fibers). This term also includes disorders such as Kearns-Sayre syndrome (KSS), Leigh's syndrome, maternally inherited Leigh's syndrome (MILS), Myogastrointestinal encephalomyopathy (MNGIE), Neuropathy, ataxia and retinitis pigmentosa (NARP), Friedreich's ataxia (FRDA), amyotrophic lateral sclerosis (ALS) and other motor neuron diseases, Hunting-ton's disease, macular degeneration, epilepsy, Alzheimer's, Leber's hereditary optic neuropathy (LHON), Progressive external ophthalmoplegia (PEO), and Pearson syndrome.

In some embodiments, a mitochondrial dysfunction or disorder may affect the central or peripheral nervous system. In some embodiments, a mitochondrial dysfunction or disorder comprises abnormal autonomic activity. In some embodiments, a mitochondrial dysfunction or disorder comprises functional gastrointestinal disorders (e.g., GI dysmotility, gastroesophageal reflux disease (i.e., GERD), small bowel disease, large bowel disease, irritable bowel syndrome, constipation, cyclic vomiting syndrome, etc.). In some embodiments, a mitochondrial dysfunction or disorder comprises chronic pain disorders (e.g., migraines, abdominal pain, myalgia, etc.). In some embodiments, a mitochondrial dysfunction or disorder comprises chronic fatigue disorders. In some embodiments, a mitochondrial dysfunction or disorder comprises chronic fatigue disorders. In some embodiments, a mitochondrial dysfunction or disorder comprises autistic spectrum disorders. In some embodiments, a mitochondrial dysfunction or disorder comprises psychiatric disorders. In some embodiments, a mitochondrial dysfunction or disorder comprises cognitive dysfunction and/or decline. In some embodiments, a mitochondrial dysfunction or disorder comprises episodic encephalopathy. In some embodiments, a mitochondrial dysfunction or disorder comprises episodic dementia/psychosis.

In some embodiments, a risk of a mitochondrial dysfunction or disorder comprises a risk from 1, 2, 3, 4, 5, 6, 7, 8, 9, 10, 15, 20, 25, 30, 35, 40, 45, 50, 55, 60, 65, 70, 75, 80, 85, 90, 95, 100, 1000% or more relative to a reference. In some embodiments, a reference comprises an average occurrence of a mitochondrial dysfunction or disorder in a population. In some embodiments, a reference comprises a statistical occurrence of a mitochondrial dysfunction or disorder deemed to be acceptable or unavoidable in a population by medical professionals.

TRAP1 Mutations

The present invention encompasses the recognition that a change-of-function mutation in nuclear DNA that encodes TRAP1 can be associated with an altered risk of or suffering from a neurological and/or mitochondrial dysfunction or disorder.

In some embodiments, a change-of-function mutation is in the regulatory sequence of the TRAP1 gene. In some embodiments, the change-of-function mutation is in the coding sequence of the TRAP1 gene. In some embodiments, the change-of-function mutation is in the ATPase domain (e.g., amino acid residues 108-260 of SEQ ID NO: 1) of the TRAP1 gene. In some embodiments, the change-of-function mutation is in the C-terminal HSP90-like domain of the TRAP1 gene (e.g., amino acid residues 292-701 of SEQ ID NO: 1). In some embodiments, the change-of-function mutation comprises a mutation of amino acid residues 165, 192, 216, 253, 266, 340, 388, 444, 455, 457, 469, 535 and/or 685 of SEQ ID NO: 1. In some embodiments, the change-of-function mutation is or comprises a mutation selected from the group consisting of 165Q>E, 192E>K, 216E>*, 253I>V, 266S>R, 340R>H, 388R>Q, 444Y>N, 455G>S, 457E>K, 469R>H, 535T>S, 685D>N, and combinations thereof.

In some embodiments, the change-of-function mutation in nuclear DNA that encodes TRAP1 causes reduced expression of a TRAP1 gene product. In some embodiments, reduced expression of a TRAP1 gene product comprises a reduction of 1, 2, 3, 4, 5, 6, 7, 8, 9, 10, 15, 20, 25, 30, 35, 40, 45, 50, 55, 60, 65, 70, 75, 80, 85, 90, 95, 100% or more relative to a reference. In some embodiments, the change-of-function mutation in nuclear DNA that encodes TRAP1 causes increased expression of a TRAP1 gene product. In some embodiments, increased expression of a TRAP1 gene product comprises an increase of 1, 2, 3, 4, 5, 6, 7, 8, 9, 10, 15, 20, 25, 30, 35, 40, 45, 50, 55, 60, 65, 70, 75, 80, 85, 90, 95, 100% or more relative to a reference. In some embodiments, a reference is a sample from an individual without a neurological and/or mitochondrial dysfunction or disorder. In some embodiments, a reference is a sample from an individual known to have a wild type TRAP1 gene.

In some embodiments, the change-of-function mutation in nuclear DNA that encodes TRAP1 causes reduced ATPase activity of a TRAP1 gene product. In some embodiments, reduced ATPase activity of a TRAP1 gene product comprises a reduction of 1, 2, 3, 4, 5, 6, 7, 8, 9, 10, 15, 20, 25, 30, 35, 40, 45, 50, 55, 60, 65, 70, 75, 80, 85, 90, 95, 100% or more relative to a reference. In some embodiments, the change-of-function mutation in nuclear DNA that encodes TRAP1 causes increased ATPase activity of a TRAP1 gene product. In some embodiments, increased ATPase activity of a TRAP1 gene product comprises an increase of 1, 2, 3, 4, 5, 6, 7, 8, 9, 10, 15, 20, 25, 30, 35, 40, 45, 50, 55, 60, 65, 70, 75, 80, 85, 90, 95, 100% or more relative to a reference. In some embodiments, a reference is a sample from an individual without a neurological and/or mitochondrial dysfunction or disorder. In some embodiments, a reference is a sample from an individual known to have a wild type TRAP1 gene.

Methods of quantifying levels of RNA transcripts are well known in the art and include but are not limited to northern analysis, semi-quantitative reverse transcriptase PCR, quantitative reverse transcriptase PCR, and microarray analysis. These and other basic RNA transcript detection procedures are described in Ausebel et al. (1998. *Current Protocols in Molecular Biology*. Wiley: New York).

In some embodiments, the change-of-function mutation causes reduced activity of a TRAP1 gene product. In some embodiments, reduced activity of a TRAP1 gene product comprises a reduction of 1, 2, 3, 4, 5, 6, 7, 8, 9, 10, 15, 20, 25, 30, 35, 40, 45, 50, 55, 60, 65, 70, 75, 80, 85, 90, 95, 100% or more relative to a reference. In some embodiments, the change-of-function mutation causes increased activity of a TRAP1 gene product. In some embodiments, increased activity of a TRAP1 gene product comprises an increase of 1, 2, 3, 4, 5, 6, 7, 8, 9, 10, 15, 20, 25, 30, 35, 40, 45, 50, 55, 60, 65, 70, 75, 80, 85, 90, 95, 100% or more relative to a reference. In some embodiments, a reference is a sample from an individual without a neurological and/or mitochondrial dysfunction or disorder. In some embodiments, a reference is a sample from an individual known to have a wild type TRAP1 gene.

Methods of quantifying activity of a TRAP1 gene product are well known in the art. Exemplary methods include but are not limited to global RNA expression measurement with microarrays or RNA-Seq (see for example, Liu D. et al., Cancer Letters, 296: pp 194-205; 2010), immunofluorescence and ATP-sepharose binding (see for example, Felts S. J. et al., Journal of Biological Chemistry, 275: pp 3305-3312; 2000).

Diagnosis of Neurological and Mitochondrial Dysfunctions or Disorders

In some embodiments, the present invention provides methods of classifying an individual at risk of or suffering from a neurological and/or mitochondrial dysfunction or disorder. In general, such methods comprise obtaining a sample of nuclear DNA from the individual; processing the sample to determine whether the individual possesses a mutation in nuclear DNA that encodes TRAP1; and classifying the individual as one that does or does not possess a mutation in nuclear DNA that encodes TRAP1.

In some embodiments, an individual at risk of or suffering from a neurological and/or mitochondrial dysfunction or disorder is a non-human animal. In some embodiments, a non-human animal is a mouse. In some embodiments, a non-human animal is a rat. In some embodiments, a non-human animal is a dog. In some embodiments, a non-human animal is a non-human primate. In some embodiments, an individual is a human. In some embodiments, a sample is obtained from an individual harboring a TRAP1 mutation. In some embodiments, a sample is obtained from an individual harboring a change-of-function mutation in nuclear DNA that encodes TRAP1 described herein.

In some embodiments, an individual at risk of or suffering from a neurological dysfunction or disorder suffers from a mitochondrial dysfunction or disorder. Many neurological dysfunctions and disorders are mitochondria driven and share common genomic malfunctions with mitochondrial dysfunctions and disorders. Mitochondrial dysfunction or disorders are degenerative diseases due to various mechanisms such as abnormality of mitochondrial DNA (deletion, point mutation, and duplication), abnormality of cellular DNA encoding mitochondrial enzymes or complex polymeric mitochondrial components, or can be induced by toxic substances or pharmaceutical products. When mitochondria-associated genes are damaged because of these reasons, various biochemical abnormalities occur.

In some embodiments, an individual possessing a mutation in their nuclear DNA that encodes TRAP1 does not possesses heteroplasmic mitochondrial DNA variants. In some embodiments, an individual possessing a mutation in their nuclear DNA that encodes TRAP1 also possesses one or more homoplasmic mitochondrial DNA variants. Methods for sequencing mitochondrial DNA are well known in the art.

In some embodiments, a sample is any sample comprising TRAP1 nuclear DNA. In some embodiments, a sample comprises cells from which nuclear DNA (e.g., not mitochondrial DNA) is or can be obtained. In some embodiments, a sample comprises cells from which mitochondrial DNA is or can be obtained. In some embodiments, a sample comprises isolated nucleic acids. In some embodiments, a sample comprises genomic DNA. In some embodiments, a sample comprises human genomic DNA.

In some embodiments, processing comprises processing a sample to detect a sequence of nuclear DNA that encodes TRAP1. In some embodiments, processing a sample comprises amplifying a target nucleic acid region of human genomic DNA encompassing a region that encodes the TRAP1 polypeptide, wherein said region includes one or more sites of change-of-function mutations that are associated with a neurological and/or mitochondrial dysfunction or disorder. In some embodiments, amplifying comprises contacting the human genomic DNA with a 5' primer under conditions such that hybridization and extension of the target nucleic acid region occur in a forward direction. In some embodiments, amplifying further comprises contacting the human genomic DNA with a 3' primer under conditions such that hybridization and extension of the target nucleic acid region occur in a reverse direction.

Nucleic acid amplification methods are well known in the art and include, but are not limited to, the Polymerase Chain Reaction (or PCR, described, for example, in U.S. Pat. Nos. 4,683,195, 4,683,202 and 4,889,818, each of which is incorporated herein by reference in its entirety). In its simplest form, PCR is an in vitro method for the enzymatic synthesis of specific DNA sequences, using two primers that hybridize to opposite strands and flank the region of interest in the target DNA. A plurality of reaction cycles, each cycle comprising: a denaturation step, an annealing step, and a polymerization step, results in the exponential accumulation of a specific DNA fragment. The termini of the amplified fragments are defined as the 5' ends of the primers. Examples of DNA polymerases capable of producing amplification products in PCR reactions include, but are not limited to: *E. coli* DNA polymerase I, Klenow fragment of DNA polymerase I, T4 DNA polymerase, thermostable DNA polymerases isolated from *Thermus aquaticus* (Taq) which are available from a variety of sources (for example, Perkin Elmer), *Thermus thermophilus* (United States Biochemicals), *Bacillus stereothermophilus* (Bio-Rad), or *Thermococcus litoralis* ("Vent" polymerase, New England Biolabs.

In some embodiments, the one or more sites of change-of-function mutations correspond to amino acids 165, 192, 216, 253, 266, 340, 388, 444, 455, 457, 469, 535 and/or 685 of a TRAP1 gene product. In some embodiments, the change-of-function mutations are selected from the group consisting of 165Q>E, 192E>K, 216E>*, 253I>V, 266S>R, 340R>H, 388R>Q, 444Y>N, 455G>S, 457E>K, 469R>H, 535T>S, 685D>N, and combinations thereof.

In some embodiments, a first amplification step amplifies a region of a target gene. In some embodiments the amplification product is less than about 3000, 2900, 2800, 2700, 2600, 2500, 2400, 2300, 2200, 2100, 2000, 1900, 1800, 1700, 1600, 1500, 1400, 1300, 1200, 1100, 1000, 900, 800, 700, 600, 500, 400, 300, 250, 225, 200, 175 or 150 nucleotides long.

In some embodiments, processing a sample comprises genotyping a nucleic acid (e.g., an amplified nucleic acid) using techniques described herein. In some embodiments, an individual is classified as at risk of or suffering from a neurological and/or mitochondrial dysfunction or disorder if they are determined by genotyping to have one or more mutant alleles. In some embodiments, mutant alleles encode a TRAP1 mutation described herein whose presence correlates with incidence and/or risk of a neurological and/or mitochondrial dysfunction or disorder.

Common genotyping methods are known in the art and include, but are not limited to, sequencing, quantitative PCR, molecular beacon assays, nucleic acid arrays, allele-specific primer extension, allele-specific PCR, arrayed primer extension, homogeneous primer extension assays, primer extension with detection by mass spectrometry, pyrosequencing, multiplex primer extension sorted on genetic arrays, ligation with rolling circle amplification, homogeneous ligation, OLA, multiplex ligation reaction sorted on genetic arrays, restriction-fragment length polymorphism, single base extension-tag assays, and the Invader assay. Such methods may be used in combination with detection mechanisms such as, for example, luminescence or chemiluminescence detection, fluorescence detection, time-resolved fluorescence detection, fluorescence resonance energy transfer, fluorescence polarization, mass spectrometry, and electrical detection.

In some embodiments genotyping nuclear DNA that encodes TRAP1 comprises sequencing the amplified DNA. In some embodiments, any of a variety of sequencing reactions known in the art can be used to directly sequence at least a portion of amplified DNA. Exemplary sequencing reactions include those based on techniques developed by Maxam and Gilbert, Proc. Natl. Acad. Sci USA, 74:560 (1977) or Sanger, Proc. Nat. Acad. Sci 74:5463 (1977). It is also contemplated that any of a variety of automated sequencing procedures may be utilized when performing the subject assays, e.g., see Venter et al., Science, 291:1304-1351 (2001); Lander et al., Nature, 409:860-921 (2001), including sequencing by mass spectrometry, e.g., see U.S. Pat. No. 5,547,835 and PCT Patent Publication No. WO 94/16101 and WO 94/21822; U.S. Pat. No. 5,605,798 and PCT Patent Application No. PCT/US96/03651; Cohen et al., Adv. Chromatogr. 36:127-162 (1996); and Griffin et al., Appl. Biochem. Biotechnol. 38:147-159 (1993). It will be evident to one skilled in the art that, for some embodiments, the occurrence of only one, two or three of the nucleic acid bases need be determined in the sequencing reaction. Yet other sequencing methods are disclosed, e.g., in U.S. Pat. Nos. 5,580,732; 5,571,676; 4,863,849; 5,302,509; PCT Patent Application Nos. WO 91/06678 and WO 93/21340; Canard et al., Gene 148:1-6 (1994); Metzker et al., Nucleic Acids Research 22:4259-4267 (1994) and U.S. Pat. Nos. 5,740,341 and 6,306,597. In some embodiments, sequencing reactions comprise deep sequencing.

In some embodiments, genotyping nuclear DNA that encodes TRAP1 comprises hybridizing a nucleic acid detection probe to the amplified DNA, wherein the nucleic acid detection probe comprises sequence that is complimentary to the sequence of the at least one mutation. In some embodiments, hybridization of the nucleic acid detection probe to the amplified human genomic DNA is detected by quantitative PCR. "Quantitative" PCR which are also referred to as "real-time PCR" and "real-time RT-PCR," respectively, involves detecting PCR products via a probe that provides a signal (typically a fluorescent signal) that is related to the amount of amplified product in the sample. Examples of commonly used probes used in quantitative include the following probes: TAQMAN® probes, Molecular Beacons probes, SCORPION® probes, and SYBR® Green probes. Briefly, TAQMAN® probes, Molecular Beacons, and SCORPION® probes each have a fluorescent reporter dye (also called a "fluor") attached on or around the 5' end of the probes and a quencher moiety attached on or around the 3' end of the probes. In the unhybridized state, the proximity of the fluor and the quench molecules prevents the detection of fluorescent signal from the probe. During PCR, when the polymerase replicates a template on which a probe is bound, the 5'-nuclease activity of the polymerase cleaves the probe at a site between the fluor and quencher thus, increasing fluorescence with each replication cycle. SYBR® Green probes bind double-stranded DNA and upon excitation emit light; thus as PCR product accumulates, fluorescence increases.

In some embodiments, the nucleic acid detection probe detect nucleic acids that encode a 165Q>E mutation of TRAP1. In some embodiments, the nucleic acid detection probe detect nucleic acids that encode a 192E>K mutation of TRAP1. In some embodiments, the nucleic acid detection probe detect nucleic acids that encode a 216E>* mutation of TRAP1. In some embodiments, the nucleic acid detection probe detect nucleic acids that encode a 253I>V mutation of TRAP1. In some embodiments, the nucleic acid detection probe detect nucleic acids that encode a 266S>R mutation of TRAP1. In some embodiments, the nucleic acid detection probe detect nucleic acids that encode a 340R>H mutation of TRAP1. In some embodiments, the nucleic acid detection probe detect nucleic acids that encode a 388R>Q mutation of TRAP1. In some embodiments, the nucleic acid detection probe detect nucleic acids that encode a 444Y>N mutation of TRAP1. In some embodiments, the nucleic acid detection probe detect nucleic acids that encode a 455G>S mutation of TRAP1. In some embodiments, the nucleic acid detection probe detect nucleic acids that encode a 457E>K mutation of TRAP1. In some embodiments, the nucleic acid detection probe detect nucleic acids that encode a 469R>H mutation of TRAP1. In some embodiments, the nucleic acid detection probe detect nucleic acids that encode a 535T>S mutation of TRAP1. In some embodiments, the nucleic acid detection probe detect nucleic acids that encode a 685D>N mutation of TRAP1.

In some embodiments genotyping nuclear DNA that encodes TRAP1 comprises a primer extension reaction. Several such methods have been described in the patent and scientific literature and include the "Genetic Bit Analysis" method (WO92/15712) and the ligase/polymerase mediated genetic bit analysis (U.S. Pat. No. 5,679,524). Related methods are disclosed in WO91/02087, WO90/09455, WO95/17676, U.S. Pat. Nos. 5,302,509, and 5,945,283. In some embodiments a primer extension reaction comprises contacting the amplified nucleic acid with one or more primers which specifically hybridize to a region of the isolated nucleic acid containing a mutation, and amplifying the hybridized amplified nucleic acid to detect the nucleotide present at the position of interest. In some embodiments detecting the presence or absence of an amplification product (assays can be designed so that hybridization and/or amplification will only occur if a particular mutation is present or absent).

Antioxidants

The present invention encompasses the recognition that inhibition of oxidative activity (e.g., oxidative stress) and/or radical oxygen species represents an effective therapy for neurological and/or mitochondrial dysfunctions or disorders, wherein nuclear DNA of the individual that encodes TRAP1 includes a change-of-function mutation. Without wishing to be bound by any particular theory, the present invention proposes that change of TRAP1 function results in an inability to degrade harmful radical oxygen species and damaging oxidative stress, manifesting as common clinical symptoms of neurological and/or mitochondrial dysfunctions or disorders (e.g., chronic fatigue, chronic pain, migraine, GI dysmotility, etc.). The present invention proposes that administration of one or more antioxidants to a subject whose TRAP1 includes a change-of-function mutation restores oxidative balance, and is an effective therapy for neurological and/or mitochondrial dysfunctions or disorders.

In some embodiments, the current invention provides methods of treating or reducing risk for a neurological and/or mitochondrial dysfunction or disorder comprising administering to a subject one or more antioxidants. In certain embodiments, the methods comprise administering to the individual a therapeutically effective amount of an antioxidant, wherein nuclear DNA of the individual that encodes TRAP1 includes a change-of-function mutation.

In some embodiments, classifying the individual as one that does or does not possess a mutation in nuclear DNA that encodes TRAP1 according to the methods described herein further comprises providing the individual or a physician treating the individual with information regarding the mutation. In some embodiments, the information references a correlation between the mutation and the potential benefits of therapy with an antioxidant.

In some embodiments, the invention described herein comprises methods of aiding in the selection of a therapy for an individual at risk of or suffering from a neurological and/or mitochondrial dysfunction or disorder, the method comprising obtaining a sample of nuclear DNA from the individual, processing the sample to determine whether the individual possesses a change-of-function mutation in nuclear DNA that encodes TRAP1, and classifying the individual as one that could benefit from therapy with an antioxidant if the step of processing determines that the individual possesses a change-of-function mutation in nuclear DNA that encodes TRAP1 using techniques described herein.

A variety of antioxidants may be used in methods of the present disclosure. Representative antioxidants include, but are not limited to Vitamin C (e.g., ascorbic acid), Vitamin A (e.g., retinol, retinal, retinoic acid, beta-carotene, etc.), Vitamin E (e.g., tocopherols, tocotrienols, etc.), polyphenols, N-acetyl cysteine, Coenzyme $Q_{10}$, alpha-tocopherol, alpha-tocotrienol (EPI-743), Idebenone and pharmaceutically acceptable salts thereof. The present invention also encompasses the use of combinations or "cocktails" of these or other antioxidants.

In some embodiments, an antioxidant is cannabidiol. Exemplary antioxidant structures are represented in Table 2.

TABLE 2

Exemplary antioxidants

| Antioxidant | Structure |
|---|---|
| N-acetyl cysteine | 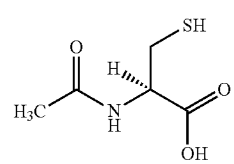 |
| Coenzyme $Q_{10}$ | 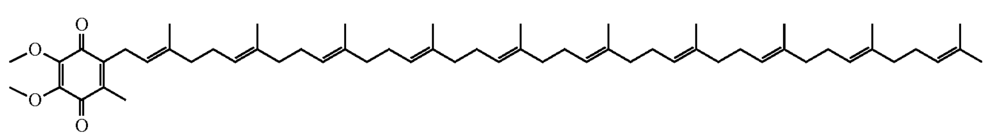 [SMILES: COC1=C(OC)C(=O)C(C/C=C(\C)CC/C=C(\C)CC/C=C(\C)CC/C=C(\C)CC/C=C(\C)CC/C=C(\C)CC/C=C(\C)CC/C=C(\C)CC/C=C(\C)CCC=C(C)C)=C(C)C1=O] |
| alpha-tocopherol | 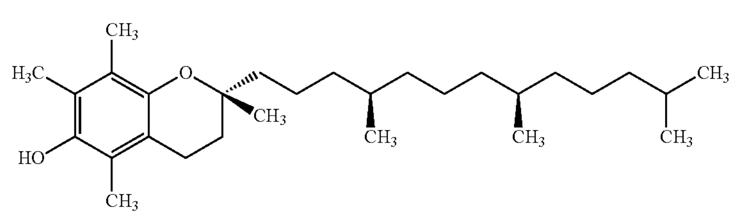 [SMILES: Cc1c(C)c2c(c(C)c1O)CC[C@@](C)(CCC[C@H](C)CCC[C@H](C)CCCC(C)C)O2] |

TABLE 2-continued

Exemplary antioxidants

| Antioxidant | Structure |
|---|---|
| alpha-tocotrienol (EPI-743) | 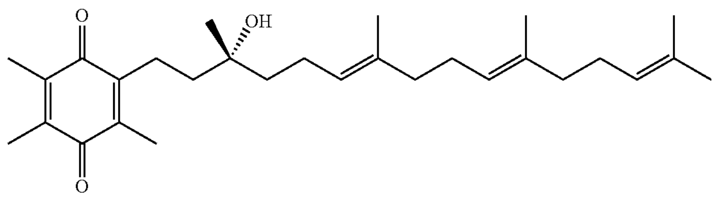 [SMILES: CC(C)=CCC/C(C)=C/CC/C(C)=C/CC[C@@](C)(O)CCC1=C(C)C(=O)C(C)=C(C)C1=O] |
| Idebenone | 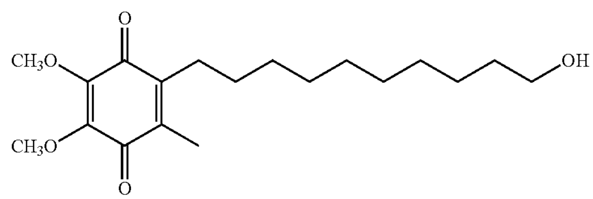 |
| cannabidiol | 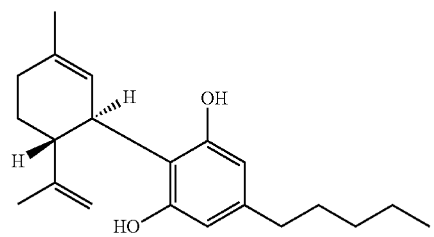 [SMILES: C=C(C)[C@@H]1CCC(C)=C[C@H]1c1c(O)cc(CCCCC)cc1O] |

In accordance with the methods of the invention, an antioxidant can be administered to a subject alone, or as a component of a composition or medicament (e.g., in the manufacture of a medicament for the prevention or treatment of a neurological and/or mitochondrial dysfunction or disorder), as described herein. The compositions can be formulated with a physiologically acceptable carrier or excipient to prepare a pharmaceutical composition. The carrier and composition can be sterile. The formulation should suit the mode of administration. Methods of formulating compositions are known in the art (see, e.g., Remington's Pharmaceuticals Sciences, $17^{th}$ Edition, Mack Publishing Co., (Alfonso R. Gennaro, editor) (1989)). Suitable pharmaceutically acceptable carriers are known in the art.

The composition or medicament, if desired, can also contain minor amounts of wetting or emulsifying agents, or pH buffering agents. The composition can be a liquid solution, suspension, emulsion, tablet, pill, capsule, sustained release formulation, or powder. The composition can also be formulated as a suppository, with traditional binders and carriers such as triglycerides. Oral formulations can include standard carriers such as pharmaceutical grades of mannitol, lactose, starch, magnesium stearate, polyvinyl pyrollidone, sodium saccharine, cellulose, magnesium carbonate, etc.

An antioxidant described herein (or a composition or medicament containing an agent described herein) is administered by any appropriate route. In some embodiments, an antioxidant is administered subcutaneously. As used herein, the term "subcutaneous tissue", is defined as a layer of loose, irregular connective tissue immediately beneath the skin. For example, the subcutaneous administration may be performed by injecting a composition into areas including, but not limited to, thigh region, abdominal region, gluteal region, or scapular region. In some embodiments, an antioxidant is administered intravenously. In some embodiments, an antioxidant is administered orally. In other embodiments, an antioxidant is administered by direct administration to a target tissue, such as heart or muscle (e.g., intramuscular), tumor (intratumorallly), nervous system (e.g., direct injection into the brain; intraventricularly; intrathecally). Alternatively, an antioxidant (or a composition or medicament containing an agent) can be administered by inhalation, parenterally, intradermally, transdermally, or transmucosally (e.g., orally or nasally). More than one route can be used concurrently, if desired.

In various embodiments, an antioxidant is administered at a therapeutically effective amount. As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating the underlying disease or condition). In some particular embodiments, appropriate doses or amounts to be administered may be extrapolated from dose-response curves derived from in vitro or animal model test systems.

In some embodiments, a composition is administered in a therapeutically effective amount and/or according to a dosing regimen that is correlated with a particular desired outcome (e.g., with treating or reducing risk for a neurological dysfunction or disorder).

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, or combinations thereof).

In some embodiments, a provided composition is provided as a pharmaceutical formulation. In some embodiments, a pharmaceutical formulation is or comprises a unit dose amount for administration in accordance with a dosing regimen correlated with achievement of the reduced incidence or risk of a neurological and/or mitochondrial dysfunction or disorder.

In some embodiments, a formulation comprising an antioxidant described herein is administered as a single dose. In some embodiments, a formulation comprising an antioxidant described herein is administered at regular intervals. Administration at an "interval," as used herein, indicates that the therapeutically effective amount is administered periodically (as distinguished from a one-time dose).

In some embodiments, a formulation comprising an antioxidant described herein is administered at regular intervals indefinitely. In some embodiments, a formulation comprising an antioxidant described herein is administered at regular intervals for a defined period.

Kits

In some embodiments, the present invention provides kits comprising materials useful for the amplification and detection or sequencing of the nuclear DNA that encompasses part or all of the TRAP1 gene product according to methods described herein. The inventive kits may be used by diagnostic laboratories, experimental laboratories, or practitioners. In some embodiments, the present disclosure provides kits further comprising materials useful for treating a neurological and/or mitochondrial dysfunction or disorder. In some embodiments, the materials useful for treating the neurological and/or mitochondrial dysfunction or disorder are antioxidants.

Materials and reagents useful for the detection or sequencing of the nuclear DNA that encompasses part or all of the TRAP1 gene product according to the present disclosure may be assembled together in a kit. In some embodiments, an inventive kit comprises at least one inventive primer set, and optionally, amplification reaction reagents. In some embodiments, a kit comprises reagents which render the procedure specific. In some embodiments, the kit comprises nucleic detection probes. Thus, a kit intended to be used for the detection of a particular change-of-function mutation (e.g., 165Q>E, 192E>K, 216E>*, 253I>V, 266S>R, 340R>H, 388R>Q, 444Y>N, 455G>S, 457E>K, 469R>H, 535T>S or 685D>N) preferably comprises primer sets and/or probes described herein that can be used to amplify and/or detect a particular TRAP1 target sequence of interest. A kit intended to be used for the multiplex detection of a plurality of TRAP1 target preferably comprises a plurality of primer sets and/or probes (optionally in separate containers) described herein that can be used to amplify and/or detect TRAP1 target sequences described herein.

Suitable amplification reaction reagents that can be included in an inventive kit include, for example, one or more of: buffers; enzymes having polymerase activity; enzyme cofactors such as magnesium or manganese; salts; nicotinamide adenide dinuclease (NAD); and deoxynucleoside triphosphates (dNTPs) such as, for example, deoxyadenosine triphospate; deoxyguanosine triphosphate, deoxycytidine triphosphate and deoxythymidine triphosphate, biotinylated dNTPs, suitable for carrying out the amplification reactions.

Depending on the procedure, the kit may further comprise one or more of: wash buffers and/or reagents, hybridization buffers and/or reagents, labeling buffers and/or reagents, and detection means. The buffers and/or reagents included in a kit are preferably optimized for the particular amplification/detection technique for which the kit is intended. Protocols for using these buffers and reagents for performing different steps of the procedure may also be included in the kit.

Furthermore, the kits may be provided with an internal control as a check on the amplification procedure and to prevent occurrence of false negative test results due to failures in the amplification procedure. An optimal control sequence is selected in such a way that it will not compete with the target nucleic acid sequence in the amplification reaction (as described above).

Kits may also contain reagents for the isolation of nucleic acids from biological specimen prior to amplification.

The reagents may be supplied in a solid (e.g., lyophilized) or liquid form. The kits of the present disclosure optionally comprise different containers (e.g., vial, ampoule, test tube, flask or bottle) for each individual buffer and/or reagent. Each component will generally be suitable as aliquoted in its respective container or provided in a concentrated form. Other containers suitable for conducting certain steps of the amplification/detection assay may also be provided. The individual containers of the kit are preferably maintained in close confinement for commercial sale.

The kit may also comprise instructions for using the amplification reaction reagents, primer sets, primer/probe sets and/or antioxidant according to the present disclosure. Instructions for using the kit according to one or more methods of the present disclosure may comprise instructions for processing the biological sample, extracting nucleic acid molecules, and/or performing the test; instructions for interpreting the results as well as a notice in the form prescribed by a governmental agency (e.g., FDA) regulating the manufacture, use or sale of pharmaceuticals or biological products.

Computer Systems

Methods described herein can be implemented in a computer system having a processor that executes specific instructions in a computer program. The computer system may be arranged to output a medication profile based on receiving an individual's genotype (e.g., TRAP1 polymorphism(s)). Particularly, the computer program may include instructions for the system to select the most appropriate medication (e.g., an antioxidant or a particular antioxidant) for an individual.

In some embodiments, the computer program may be configured such that the computer system can identify the genotype based on received data and provide a preliminary identification of the universe of possible medications. The system may be able to rank-order the identified medications based on specific co-factors in the algorithmic equation. The system may be able to adjust the rank ordering based on the genotypic polymorphism(s) carried by the individual. The system may be able to adjust the rank ordering based on clinical responses, such as by family members of the individual.

FIG. 1 is a block diagram of a computer system 100 that can be used in the operations described above, according to one embodiment. The system 100 includes a processor 110, a memory 120, a storage device 130 and an input/output device 140. Each of the components 110, 120, 130 and 140 are interconnected using a system bus 150. The system may include analyzing equipment 160 for determining the individual's genotype.

The processor 110 is capable of processing instructions for execution within the system 100. In one embodiment, the processor 110 is a single-threaded processor. In another embodiment, the processor 110 is a multi-threaded processor. The processor 110 is capable of processing instructions stored in the memory 120 or on the storage device 130, including for receiving or sending information through the input/output device 140.

The memory 120 stores information within the system 100. In one embodiment, the memory 120 is a computer-readable medium. In one embodiment, the memory 120 is a volatile memory unit. In another embodiment, the memory 120 is a non-volatile memory unit.

The storage device 130 is capable of providing mass storage for the system 100. In one embodiment, the storage device 130 is a computer-readable medium. In various different embodiments, the storage device 130 may be a floppy disk device, a hard disk device, an optical disk device, or a tape device.

The input/output device 140 provides input/output operations for the system 100. In one embodiment, the input/output device 140 includes a keyboard and/or pointing device. In one embodiment, the input/output device 140 includes a display unit for displaying graphical user interfaces.

Figure 2:
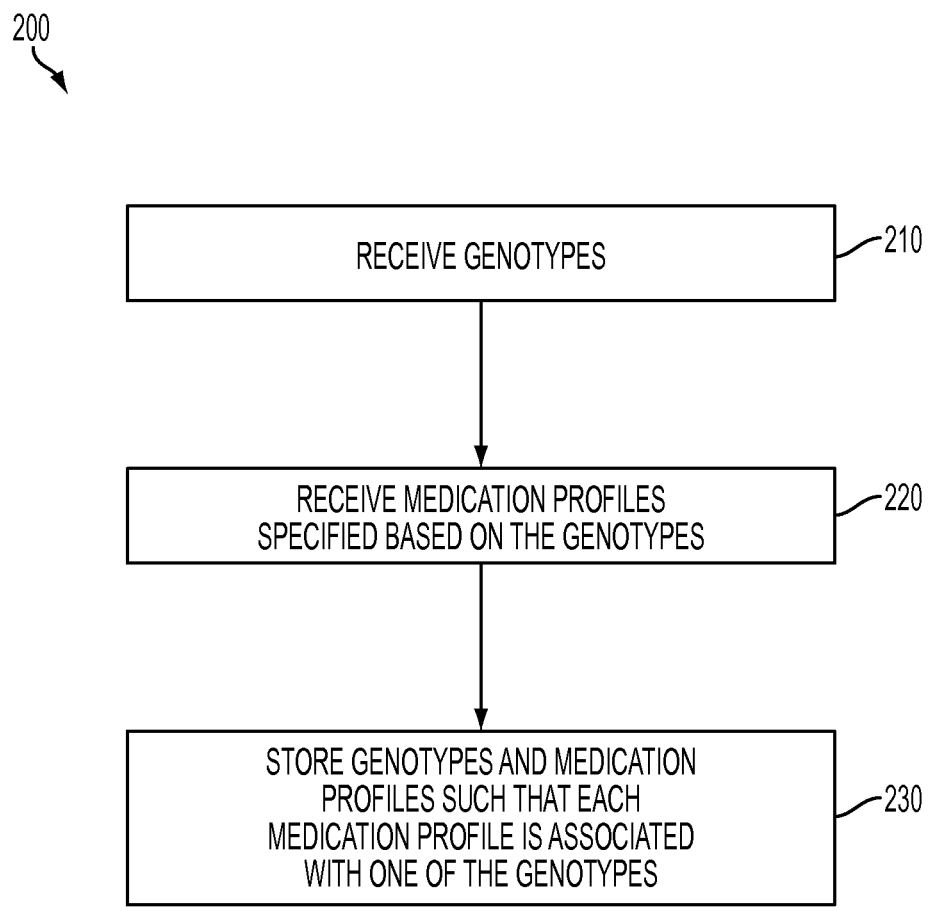
FIG. 2: depicts an exemplary flow chart of a method 200 for building a database for use in selecting a medication for a patient.

The system 100 can be used to build a database. FIG. 2 shows a flow chart of a method 200 for building a database for use in selecting a medication for an individual. Preferably, the method 200 is performed in the system 100. For example, a computer program product can include instructions that cause the processor 110 to perform the steps of the method 200. The method 200 includes the following steps.

Receiving, in step 210, a plurality of genotypes 170 for TRAP1. A computer program in the system 100 may include instructions for presenting a suitable graphical user interface on input/output device 140, and the graphical user interface may prompt the user to enter the genotypes 170 using the input/output device 140, such as a keyboard.

Receiving, in step 220, a plurality of medication profiles 180. The medication profiles 180 are specified based on the genotypes 170. The user may enter the medication profiles 180 using the input/output device 140, such as a keyboard. For example, the medication profile 180 may include information 190 regarding at least one medication.

Storing, in step 230, the received genotypes 170 and the medication profiles 180 such that each medication profile 180 is associated with one of the genotypes 170. The system 100 may store the medication profiles 180 and the genotypes 170 in the storage device 130. For example, when the storing is complete, the system 100 can identity a particular one of the medication profiles 180 that is associated with a specific genotype 170. Having identified the medication profile 180, the system 100 can access the information 190 contained within the identified medication profile 180, as will be described in the following example.

Figure 3:
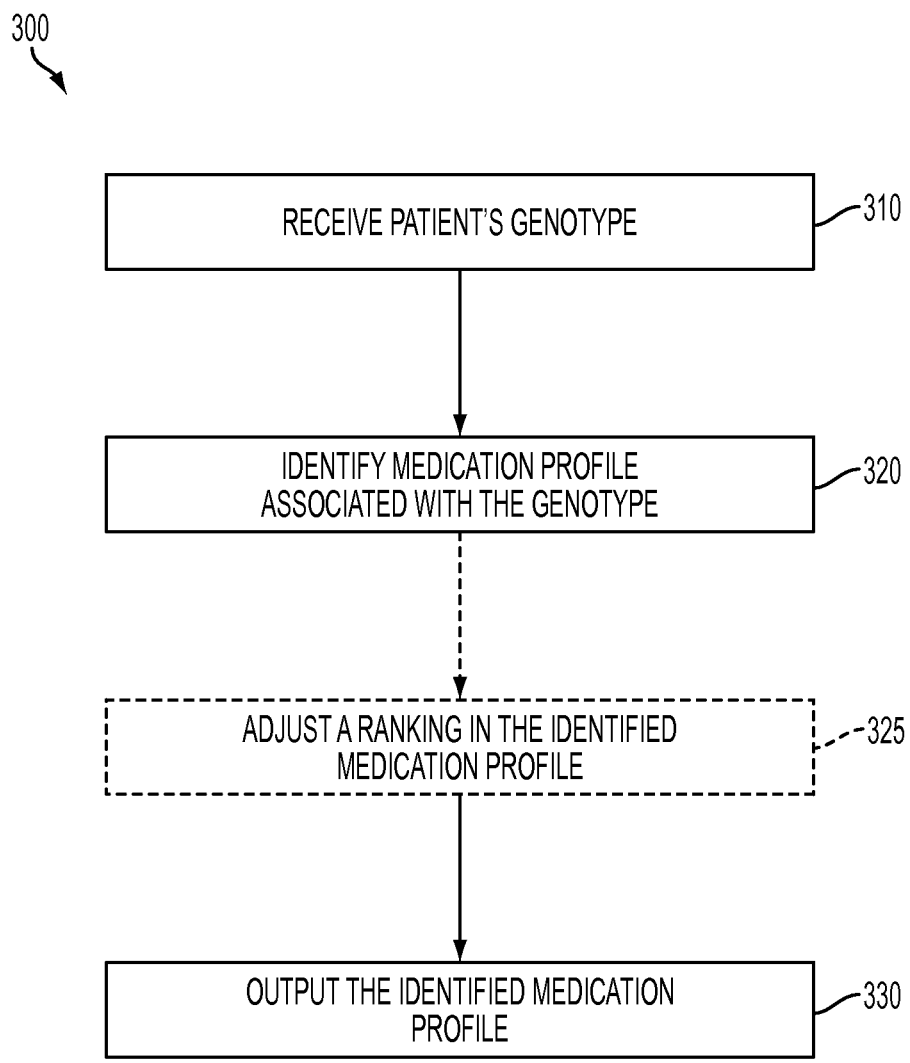
FIG. 3: depicts an exemplary flow chart of a method 300 for selecting medication for a patient.

The system 100 may be used for selecting a medication. FIG. 3 shows a flow chart of a method 300 of selecting a medication for an individual. Preferably, the method 300 is performed in the system 100. For example, a computer program product can include instructions that cause the processor 110 to perform the steps of the method 300. The method 300 includes the following steps.

Receiving, in step 310, an individual's genotype for TRAP1. The genotype may be entered by a user via input/output device 140. For example, the user may obtain the individual's genotype for TRAP1 using the analyzing equipment 160 (which may or may not be connected to the system 100). The user may type the individual's genotype on input/output device 140, such as a keyboard, for receipt by the system 100.

The genotype may be received directly from the analyzing equipment 160. For example, analyzing equipment 160 may include a processor and suitable software such that it can communicate over a network. The system 100 may be connected to the analyzing equipment 160 through input/output device 140, such as a network adapter, and directly receive the individual's genotype.

Identifying, in step 320, one of the medication profiles 180 that is associated with the individual's genotype. For example, the system 100 may perform a database search in the storage device 130. Particularly, the system 100 may access the genotype 170 for individual medication profiles 180 until a match is found. Optional step 325 will be described below.

Outputting, in step 330, the identified medication profile 180 in response to receiving the individual's genotype. The system may output the identified medication profile 180 through input/output device 140. For example, the identified medication profile may be printed or displayed in a suitable graphical user interface on a display device. As another example, the system 100 may transmit the identified medication profile over a network, such as a local area network or the Internet, to which the input/output device 140 is connected.

The medication profiles 180 can be created such that there is flexibility in how the system 100 outputs them. For example, the information 190 in one or more of the medication profiles 180 may include a ranking of several medications. The program may include instructions for applying rules to the received individual's genotype and adjust the ranking accordingly. In such implementations, the method 300 may include optional step 325 of adjusting the ranking before outputting the identified medication profile. For example, the system 100 may receive a genotypic polymorphism carried by the individual (optionally in the same way the individual's genotype was received) and adjust the ranking accordingly in step 325. As another example, step 325 may involve adjusting the ranking based on a clinical response. The clinical response may be received by the system 100 in the same way as the individual's genotype. For example, the ranking can be adjusted based on a clinical response by a member of the individual's family.

The medication profiles 180 may be updated as necessary. For example, the introduction of a new medication on the market may prompt a revision of one or more existing medication profiles. A new medication may also be the basis for creating a new medication profile. The adjustment or creation of medication profiles may be done substantially as described above.

The medication profiles 180 may be used for medication selection in the same system where they were created, or in a different system. That is, the system 100 may first be used for building a database of the medication profiles 180, and the system 100 may thereafter be used to select a medication profile for the genotype of a specific individual. As another example, one or more medication profiles 180 may be transmitted within a computer readable medium such as a global computer network for remote processing according to the invention.

EXEMPLIFICATION

Example 1

Novel Disease Associations and Novel Disease-Associated

Genes Elucidated Among MitoCarta Gene Sequencing in 183 Probands With the advent of NextGen® DNA sequencing in the diagnosis of mitochondrial disease, has come the realization that many patients do not have a clear diagnosis. Perhaps the most likely explanation is that many cases are due to polygenic/multifactorial pathogenesis, as is the case in most fields of medicine. To elucidate novel associations, post-testing data analysis is key. Comprehensive sequencing of ~1100 nuclear genes was performed in 183 unrelated patients with a clinical suspicion of mitochondrial disease (nucSEEK®). To limit type II errors due to multiple comparisons, candidates were first assigned based on an increased prevalence of deleterious-predicted variants among patients in comparison to prevalence rates from 1000 Genomes and/or in-house negative controls. Second, the phenotype of those carrying the variant(s) were compared to the phenotypes in a "referral group" of 50 randomly-selected patients. One of the identified genes, TRAP1, was not previously associated with disease. TRAP1 encodes a mitochondrial chaperone. The TRAP1 ATPase domain has four ATP binding sites and includes amino acids 108-260. In 6 probands, three deleterious-predicted variants in that domain were detected. All 6 share a phenotype of chronic fatigue, pain and GI disease, but with normal intelligence, versus 14/50 in the referral group (p=0.001).

Example 2

Clinical Manifestations of TRAP1 Variants

TRAP1 encodes a mitochondrial chaperone, which assists in the folding of other proteins. Missense mutation in a chaperone could result in the misfolding of proteins, and thus demonstrate dominant inheritance. For example, autosomal dominant mutations in chaperone proteins cause early-onset torsion (DYT1) and myofibrillar myopathy (CRYAB). Two subsets of patients with variants within in TRAP1 were found. In six patients with chronic fatigue, pain and GI disease but with normal cognition, three different variants were detected. These variants are all located within the middle domain of TRAP1 which contains the ATPase activity. Three different mutations were detected in five patients with cognitive delay, only one of whom had functional symptoms. All these variants were located in the carboxy terminal domain. The association of the TRAP1 mutations and phenotype is highly significant (p=0.002). Results are shown in Table 3. Table 4 shows an evolutionary assessment of the TRAP1 variant, indicating the number of alignments out of those tested that matched, and how far back in the evolutionary tree the variant was found. Also indicated in Table 4 are the prevalence of the variant in the population, and an assessment of protein function with the indicated mutation.

TABLE 3

Clinical Symptoms of TRAP1 Variants

| Patient | Variant | |
|---|---|---|
| | | Outside ATPase Domain |
| 1 | R469H | no clinical information provided |
| 2 | R469H | siblings, both with severe PANS and OCD; one also with psychosis, anorexia, growth failure |
| 3 | R469H | ASD, loss of milestones, anxiety, severe OCD with sudden onset of symptoms |
| 4 | R469H | primordial growth retardation, in-utero stroke, functional disease (GI/feeding issues, fatigue, dysautonomia) |
| 5 | R469H | Leigh disease: seizures, hypotonia, developmental delay, loss of milestones, abnormal movements, abnormal organic acids |
| 6 | Y444N | no clinical information provided |
| 7 | Y444N | developmental delays, hypotonia, seizures, G-tube dependence |
| 8 | Y444N | neuromuscular disease (developmental delay, ADD/ADHD, hypotonia and skeletal muscle weakness), abnormal blood acylcarnitines, carnitine deficiency |
| 9 | Y444N | previously progressive ataxia that improved on cofactor therapy, mild skeletal myopathy, attention deficit disorder versus high functioning autism spectrum disorder, and normal to advanced intelligence |
| 10 | Y444N | autistic spectrum disorder, anxiety/panic, and hypotonia |
| 11 | R388Q | developmental delay, hypotonia, ataxia, GERD, oculomotor apraxia, Chiari type I malformation |
| 12 | S266R | neuromuscular disease (developmental delay, ADD/ADHD, hypotonia and skeletal muscle weakness), abnormal blood acylcarnitines, carnitine deficiency |
| 13 | D685N | dystonia, ataxia, peripheral neuropathy, optic neuropathy, renal stones |
| 14 | R340H | narcolepsy and Tourette syndrome |
| 15 | T535S | encephalopathy (global delay, hyptonia, anxiety disorder), muscle fatigue/poor endurance, GERD/chronic respiratory problems |
| 16 | G445S | no clinical information provided |
| 17 | E457K | no clinical information provided |
| | | Inside ATPase domain |
| 18 | I253V | no clinical information provided |
| 19 | I253V | autism, developmental delay, depression, seizures, gastrointestinal dysmotility (large bowel), chronic headaches, chronic fatigue, exercise intolerance |
| 20 | I253V | chronic fatigue syndrome, including chronic pain and insomnia. Additional functional symptomatology of periodic fever, |

TABLE 3-continued

Clinical Symptoms of TRAP1 Variants

| Patient | Variant | |
|---|---|---|
| | | gastrointestinal dysmotility at different levels, postural orthostatic tachycardia syndrome |
| 21 | I253V | cyclic vomiting, chronic pain, chronic fatigue, POTS/syncope, tinnitus, gastrointestinal dysmotility, neuropathy and myopathy (ocular) |
| 22 | I253V | stroke-like episodes, IBS, migraines, hyperextensibility, fatigue with waxing and waning energy level |
| 23 | I253V | autistic disorder and OCD, with mycoplasma and Streptococcus group A |
| 24 | I253V | developmental delay, hypotonia, chronic pain ("neuropathic pain" in hands and feet, migraine), chronic fatigue. Lactic acid was elevated in blood, and complex I deficiency was noted in muscle |
| 25 | I253V | 3.3 Mb duplication of chromosome 12q24.13 including PTPN11, SBX3, and SBX5, with Noonan syndrome, growth hormone deficiency, borderline intellectual disability, and anxiety |
| 26 | Q165E | chronic-fatigue syndrome-like phenotype including: elevated lactate, low coenyzme Q10 level, and improvement with mitochondrial cocktail |
| 27 | Q165E | abnormal movements (possibly paroxysmal dyskinesia), ADD/ADHD, POTS/syncope, depression, chronic fatigue, cyclic vomiting |
| 28 | E192K | autism, developmental delay, depression, seizures, gastrointestinal dysmotility (large bowel), chronic headaches, chronic fatigue, exercise intolerance |
| 29 | E192K | Asperger, long history of leg pains/arm aches, not feeling his legs upon awakening, shaking when hungry or cold, stomach aches, burning skin, possible migraines, "passing out", anxiety/panic, exercise intolerance |
| 30 | E216* | tachycardia, migraine, abdominal pain, chronic fatigue and GERD, hypotonia, muscle weakness, hypoglycemia, pancreatitis |
| | | Outside ATPase domain (Negative control) |
| 31 | R469H | |
| 32 | R269W | |
| 33 | R469H | |

TABLE 4

Prevalence and evolutionary assessment of TRAP 1 variants

| Patient | Variant | Evolutionary conserved | Protein function | Prevalence | Notes |
|---|---|---|---|---|---|
| Outside ATPase Domain | | | | | |
| 1 | R469H | 39/39 - Zebrafish | O/O/O/O | 0% | |
| 2 | R469H | 39/39 - Zebrafish | O/O/O/O | 0% | |
| 3 | R469H | 39/39 - Zebrafish | O/O/O/O | 0% | |
| 4 | R469H | 39/39 - Zebrafish | O/O/O/O | 0% | |
| 5 | R469H | 39/39 - Zebrafish | O/O/O/O | 0% | Homozygous |
| 6 | Y444N | 41/41 - Zebrafish | O/O/Y/O | 0.22% | |
| 7 | Y444N | 41/41 - Zebrafish | O/O/Y/O | 0.22% | |
| 8 | Y444N | 41/41 - Zebrafish | O/O/Y/O | 0.22% | |
| 9 | Y444N | 41/41 - Zebrafish | O/O/Y/O | 0.22% | |
| 10 | Y444N | 41/41 - Zebrafish | O/O/Y/O | 0.22% | |
| 11 | R388Q | 38/38 - Zebrafish | O/O/Y/Y | 0% | |
| 12 | S266R | 36/36 - Xenopus | O/G/Y/O | 0% | A in fish |
| 13 | D685N | 38/38 - Zebrafish | O/G/Y/Y | 0.31% | |
| 14 | R340H | 41/41 - Zebrafish | O/G/G/O | 0% | |
| 15 | T535S | 40/40 - Zebrafish | O/G/G/O | 1.23% | |
| 16 | G445S | 41/41 - Zebrafish | O/G/G/O | 0% | |
| 17 | E457K | 38/41 - Zebrafish | O/G/G/O | 0% | D in Marmoset, Tenrec, Opossum |
| Inside ATPase domain | | | | | |
| 18 | I253V | 38/39 - Zebrafish | O/G/G/Y | 0.63% | V in Xenopus |
| 19 | I253V | 38/39 - Zebrafish | O/G/G/Y | 0.63% | V in Xenopus |
| 20 | I253V | 38/39 - Zebrafish | O/G/G/Y | 0.63% | V in Xenopus |
| 21 | I253V | 38/39 - Zebrafish | O/G/G/Y | 0.63% | V in Xenopus |
| 22 | I253V | 38/39 - Zebrafish | O/G/G/Y | 0.63% | V in Xenopus |
| 23 | I253V | 38/39 - Zebrafish | O/G/G/Y | 0.63% | V in Xenopus |
| 24 | I253V | 38/39 - Zebrafish | O/G/G/Y | 0.63% | V in Xenopus |

TABLE 4-continued

Prevalence and evolutionary assessment of TRAP 1 variants

| 25 | I253V | 38/39 - Zebrafish | O/G/G/Y | 0.63% | V in Xenopus |
| 26 | Q165E | 26/32 - Zebrafish | Y/G/G/O | 0% | Exclude |
| 27 | Q165E | 26/32 - Zebrafish | Y/G/G/O | 0% | Exclude |
| 28 | E192K | 39/42 - Zebrafish | O/G/G/G | 0.31% | A in microbat, D in armadillo and Xenopus |
| 29 | E192K | 39/42 - Zebrafish | O/G/G/G | 0.31% | A in microbat, D in armadillo and Xenopus |
| 30 | E216* | N/A | N/A | 0% | |

Outside ATPase domain (Negative Control)

| Patient | Variant | Evolutionary conserved Denominator - 41 | Protein function | Prevalence | Notes |
|---|---|---|---|---|---|
| 31 | R469H | 39/39 - Zebrafish | O/O/O/O | 0% | |
| 32 | R269W | 39/39 - Zebrafish | O/O/O/O | 0% | |
| 33 | R469H | 39/39 - Zebrafish | O/O/O/O | 0% | |

Note:
Severity of damaging mutations was measured by Mutation Taster (www.softgenetics.com/mutationSurveyor.html), PolyPhen (genetics.bwh.harvard.edu/pph2/), Mutation Survey (mutationassessor.org) and SIFT (sift.jcvi.org). Protein function data in column three are annotated in the same order (i.e., Mutation Taster/PolyPhen/Mutation Surveyor/SIFT). Protein function symbols are Orange, Yellow, Green. O/O/O/O is most damaging; G/G/G/G is least damaging.

Example 3

Mutations in the ATPase Domain of TRAP1 in Patients with a Triad of Functional Symptoms, Including Pain, Fatigue, and Gastrointestinal (GI) Dysmotility Patients with mitochondrial disease commonly present with functional disorders, such as chronic fatigue, migraine, irritable bowel syndrome, depression, fibromyalgia, and complex regional pain. Using Courtagen Life Sciences, Inc.'s Next Generation (NextGen®) sequencing panels, ten cases with a triad of chronic fatigue, chronic pain, and gastrointestinal dysmotility were identified to have variants of interest in the ATPase domain of the TRAP1 gene that encodes tumor necrosis factor receptor-associated protein 1, a mitochondrial chaperone involved in antioxidant defense.

Results 270 patients were referred to the inventors that presented clinical pictures typically found in connection with mitochondrial diseases, or aspects of such clinical pictures. Among these 270 patients referred to the inventors for NextGen® sequencing analysis, a significant variant in the TRAP1 gene was identified in 27 patients (10%) (Table 1 below). Genotype-phenotype correlation revealed that functional symptomatology was predominately limited to the twelve patients (4%) in which the variant was located in the ATPase domain of the TRAP1 protein (amino acids 108 to 260). Sufficient clinical information was available regarding ten of these twelve patients (Table 1 below). Six of the ten patients were female. The ages of the ten patients ranged from three to thirty years; the average age was fourteen years.

TABLE 1

Mutations Identified within the TRAP1 ATPase Domain in 10 patients

| Mutation | Nucleotide change | Position | n | % | Pop. Freq. (1000 Genomes)[a] | Evolutionary Conservation (Vertebrates)[b] | In Silico Predictions [c] |
|---|---|---|---|---|---|---|---|
| I253V | T > C | 3726094 | 8 | 80 | 0.63% | 38/39 with isoleucine, through zebrafish | Damaging/ Benign/Benign/ Uncertain |
| E192K | C > T | 3727629 | 2 | 20 | 0.31% | 39/42 with glutamate, through zebrafish | Damaging/ Benign/Benign/ Benign |
| E216X | C > A | 3727557 | 1 | 10 | 0.00% | Stop codon | Stop codon |
| Total: | | | 11[d] | 100% | | | |

[a]Frequency reported in 1000 Genomes (www.1000 genomes.org/)
[b]UCSC Genome Browser (genome.ucsc.edu)
[c] MutationTaster/Polyphen2/MutationAssessor/SIFT
[d]One patient carried both I253V and E192K It is proposed that this combination of chronic fatigue, chronic pain, and gastrointestinal dysmotility characterizes a new and likely treatable condition: TRAP1-Related Disease (T1ReD).

According to the records provided to the inventors, eight of the ten patients experienced a functional disease triad of chronic pain, chronic fatigue or exercise intolerance, and gastrointestinal (GI) dysmotility, whereas only ten of the 95 patients in the referral population control group had this triad of symptoms (P=3×10⁻⁷, OR 34, 95% CI 6-180). The two patients with an ATPase domain mutation who did not have the complete triad each exhibited two of the three symptoms (one patient did not have significant pain, and the other patient did not have GI disturbance). Eight of those ten patients had the same ATPase domain variant, I253V, which was identified at a statistically higher rate than predicted based on the 1000 Genomes frequency of 0.63% (P=0.003, OR 4.8, 95% CI 2.3-10). Among the seventeen patients with significant TRAP1 variants outside the ATPase domain (five each with Y444N and R469H, and one each with S266R, R340H, R388Q, G445S, E457K, T535S, and D685N), only one displayed the functional symptom triad of pain, fatigue, and GI dysmotility (P=0.0001, OR 64, 95% CI 5-800, v. in-domain mutations). Rather, these patients presented with varying symptoms across the spectrum of mitochondrial disease. We did not find variant I253V, or any other conserved TRAP1 ATPase variant, among 50 normal control patients assayed by the same methodologies in our laboratory.

The "functional triad" of fatigue, pain, and GI dysmotility is significantly more common among patients with conserved TRAP1 ATPase variants than in representative groups of patients referred to our laboratory for mitochondrial gene sequencing (~30 fold), as well as in our patients with conserved variants outside of the TRAP1 ATPase domain (~60 fold). While the functional triad is helpful to establish statistical significance and in identifying patients at risk for TRAP1-related disease, the associated phenotype appears to be much broader, as is clear from the case reports, likely at least including additional functional/autonomic manifestations, such as tachycardia and temperature instability.

The I253V variant in the TRAP1 ATPase domain is not rare as it is present in one in 160 people in the general population. Unlike rare genetic disease, for which one would not expect related mutations to be present in the general population, functional disease, including fatigue, pain and gut dysmotility, is relatively common Therefore, the presence of TRAP1 mutations among sequences comprising the 1000 Genomes database is, in hindsight, not surprising.

I253V shows a five-fold statistically significant enrichment among the samples with a suspicion of mitochondrial disease sent to our laboratory for NextGen sequencing. Despite exchanging one branched-chain amino acid for another, isoleucine for valine, and resulting from a single nucleotide transition (T>C), I253V is highly conserved, with the isoleucine present in 38/39 vertebrate species extending down to zebrafish (Table 1 above).

Among the ten cases with predicted TRAP1 ATPase domain mutations, the phenotypes overlapped considerably, which is reflected by the case reports below.

Case Report 1

Figure 4:
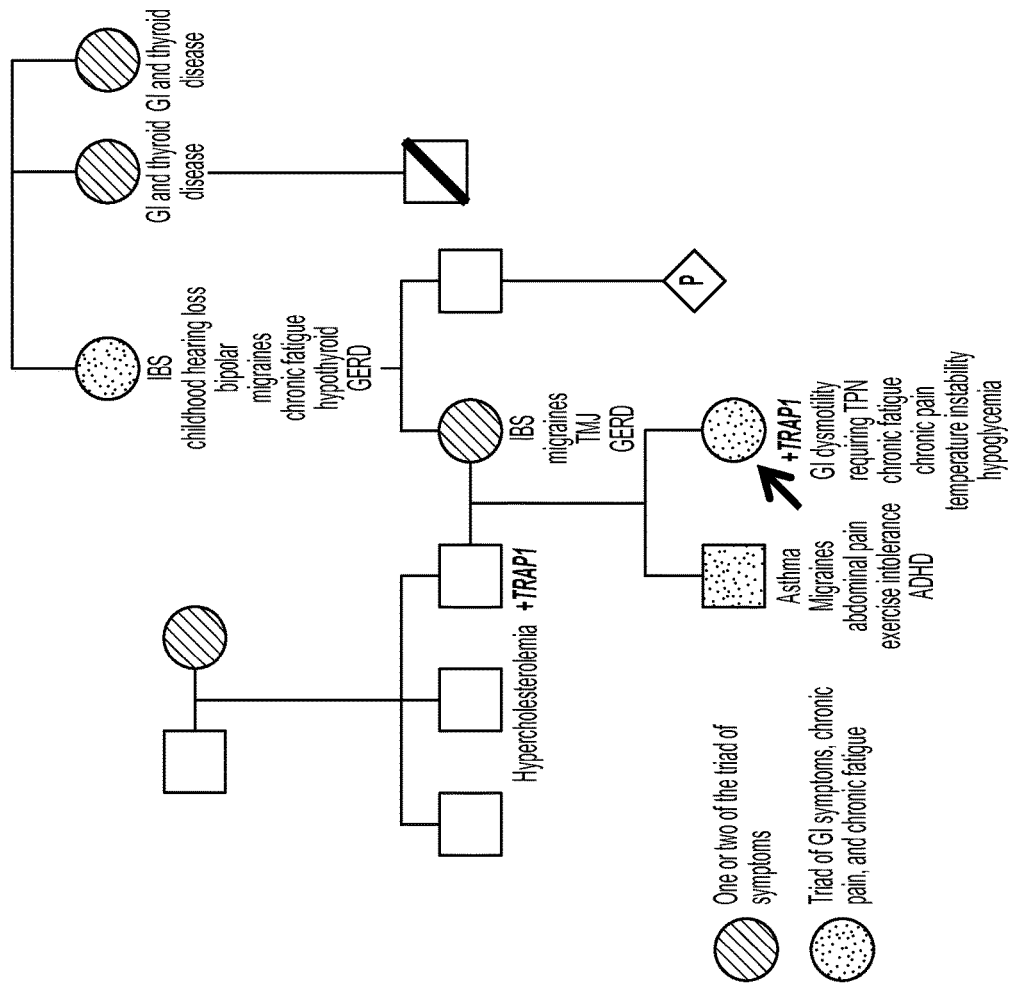
FIG. 4: depicts the genetic pedigree chart of the patient in case report no. 1.

A 4-year-old female was referred to the inventors at age one year because of a failure-to-thrive and hypoglycemia. Additional problems included constipation, temperature instability, tachycardia, delayed gastric emptying (confirmed by Scintiscan), almost-daily pain (headaches, abdominal pain, leg cramps), chronic fatigue (sleeping up to 22 hours a day), anemia (requiring multiple transfusions), repetitive episodes of right arm dyskinesia (2 minutes each, twice a week), and neurodevelopmental issues (gross motor delay, auditory processing problem, and memory defects, but cognitive delay is only 6 months). Pain, fatigue, and temperature instability responded substantially to administration of an antioxidant "cocktail", including ubiquinone, alpha lipoic acid, and vitamins C and E, as well as the additional mitochondrial targeted therapies of L-carnitine and vitamins B2 and B7. Episodic dyskinesia later resolved with L-arginine supplementation. However, gastrointestinal dysfunction worsened, necessitating a gastrostomy tube, followed by a jejunostomy tube. By age 3 years, the patient required total parental nutrition as even small volumes given orally or via tube resulted in severe discomfort and bloating. Pertinent results of an extensive work-up include normal brain MR, normal video-EEG, severe free carnitine deficiency (<4 micromolar, normal >19; total carnitine 17), trace elevations on urine organic acids, respiratory alkalosis (hyperventilation), and hypoglycemia (even while receiving adequate jejunal feeds or parental nutrition). Muscle biopsy revealed increased variation in muscle fibers sizes, focal areas of mitochondrial accumulation, mild increase in glycogen and lipids, mitochondria that were often enlarged and pleomorphic on ultrastructure, and low rotenone-sensitive NADH-cytochrome c reductase deficiency at 7% (from CIDEM, Cleveland, Ohio) with otherwise normal complexes I-IV and citrate synthase 79%). The patient's family history is shown in FIG. 4. After finding the I253V in the TRAP1 ATPase domain, antioxidant therapy was intensified, and results are pending.

Case Report 2

Figure 5:
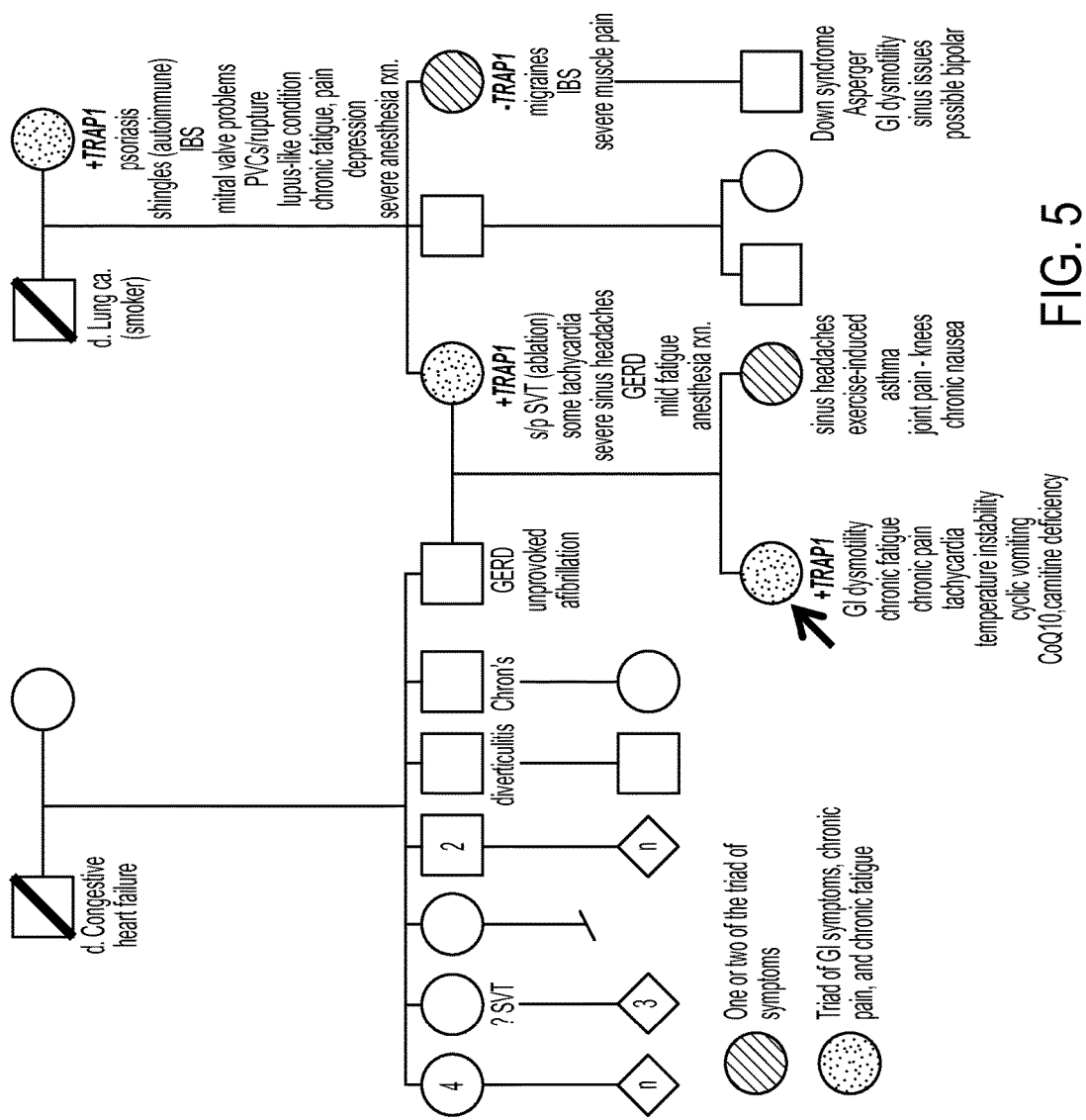
FIG. 5: depicts the genetic pedigree chart of the patient in case report no. 2.

An 18-year-old female was referred to the inventors at age 16 years because of chronic fatigue and pain. The patient met diagnostic criteria for chronic fatigue syndrome, including long-standing fatigue that precluded attendance in school, post-exertional fatigue, non-refreshed sleep, poor memory, insomnia, exercise intolerance, and chronic pain in the head, muscles, joints, throat, and (tender) lymph nodes. Additional problems included temperature instability (periodic fever up to 41° C.), gastrointestinal dysmotility (gastroesophageal reflux disease (GERD), gastroparesis, and pseudo-obstruction requiring dozens of admissions for obstruction starting at 5 years old), and postural orthostatic tachycardia syndrome. The patient's cognition was normal. Pertinent results of an extensive work-up included the following normal testing: periodic fever panel (sequencing by GeneDx, Gaithersberg, Md.), Holter monitor, urine organic acids, and alpha galactosidase activity. The family history is shown in FIG. 5. After finding the I253V in the TRAP1 ATPase domain, antioxidant therapy was instituted, and results are pending.

Case Report 3

Figure 6:
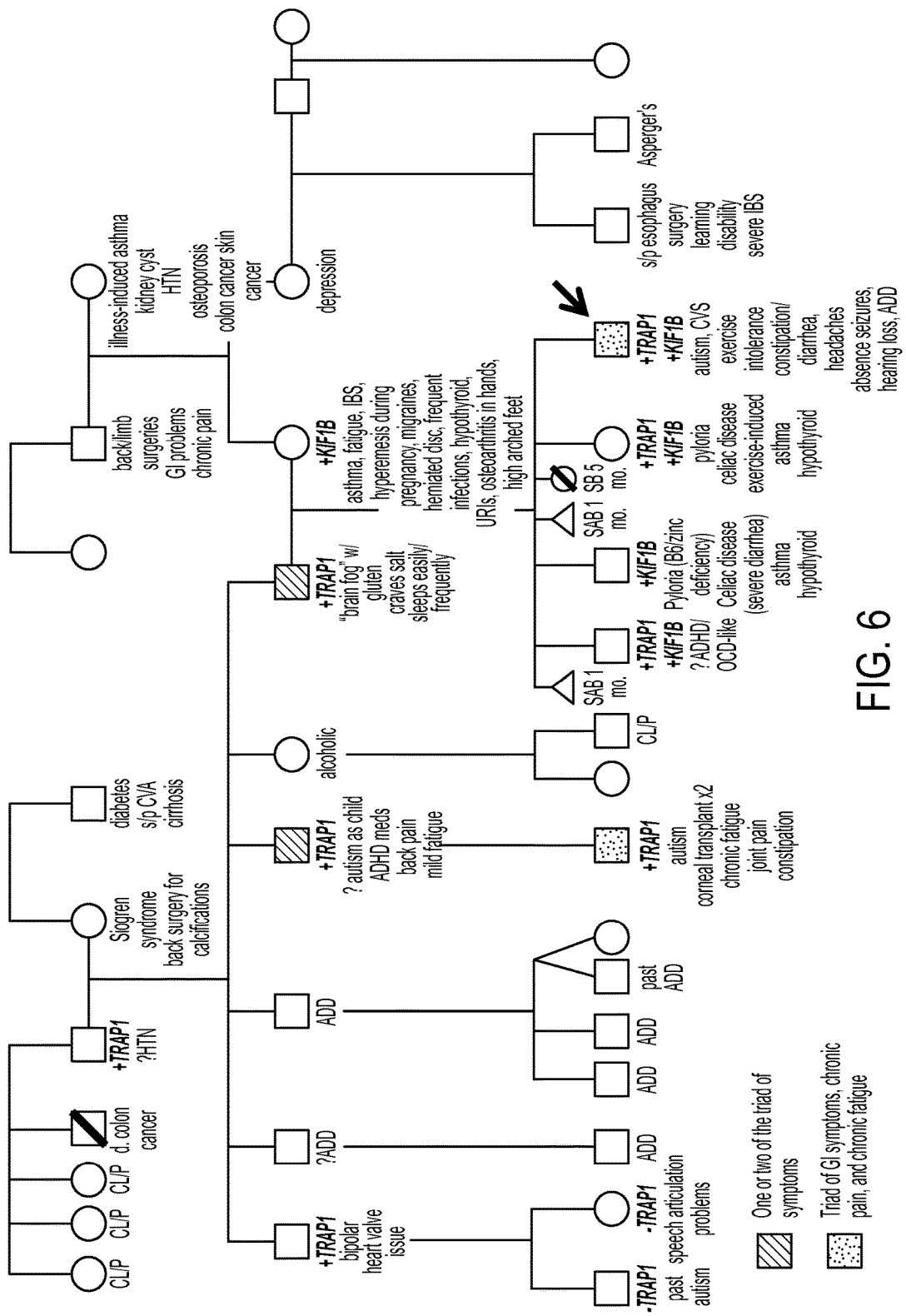
FIG. 6: depicts the genetic pedigree chart of the patient in case report no. 3.

A 13-year-old male was referred to the inventors because of autism and an additional history including absence seizures, hearing loss, attention deficit disorder, ocular apraxia, exercise intolerance, alternating constipation and diarrhea, chronic headaches, cyclic vomiting syndrome, and "PANDAS". Analysis of urine organic acids revealed the presence of elevated ketones and dicarboxylic acids levels. Microarray analysis revealed a deletion of the chromosomal region Yq12. Urine organic acids performed at Metametrix during an illness revealed elevated 3OH-butyrate and adipate. Plasma acylcarnitines were normal and plasma carnitines were 41/35/6 in November 2010 and Coenzyme Q10 was reduced 97% (5548) and plasma carnities were 79/64/15 in October 2012. In addition to the R128H variant in TRAP1 that was identified, a variant in KIF1B was identified. Parental testing revealed paternal inheritance of TRAP1 and maternal inheritance of KIF1B (FIG. 6).

Case Report 4

A 2-year, 4-month-old female with a clinical diagnosis of Leigh's disease was referred to the inventors for testing to determine a molecular cause of her disease. The patient's development was normal until 5 months of age, at which point she developed episodes of screaming her mother described as mildly seizure-like. She also developed weakness in her neck and took less formula during feedings. She was diagnosed with failure to thrive and had elevated lactate. An MRI of the brain showed atrophy consistent with Leigh's disease. Subsequently, the patient developed hypotonia, clonic and absence seizures, required a g-tube for feeding and lost milestone such as smiling. An MRI performed at 9 months of age revealed progressive brain atrophy. NucSEEK® testing determined that this patient was homozygous for the mutation R469H, which falls outside of the TRAP1 ATPase domain. Carrier confirmations in the non-consanguinous parents revealed each of them to be a carrier. Neither parent was affected with any symptom of the functional triad, and a 3-generation family history was non-contributory. NextGen® sequencing of the mtDNA by Courtagen (mtSEEK™) revealed two homoplasmic mtDNA SNPs of unclear significance (TRND 7559A>G, and ND5 13117A>G=Ile261Val) and a sporadic inheritance pattern. In silico algorithms predict this variant as being deleterious based on being very rare (not in the 1000 Genomes database, despite being identified in heterozygous status in 5 of our 270 patients), very-highly evolutionarily conserved, and predicted to be damaging by per 4 of 4 computer algorithms of protein function.

Without wishing to be limited to this particular theory, we hypothesize that the TRAP1 mutations disclosed herein exert a dominant effect resulting in inappropriate protein processing involved in antioxidant defenses, which predisposes towards the development of functional disease symptomatology, particularly on a permissive mtDNA background.

Methods

DNA was extracted from saliva samples using the SPRI-TE nucleic acid extractor and the SPRI-TE gDNA extraction kit (Beckman Coulter, Brea, Calif.) according to the manufacturer's protocols. Sequence-ready libraries for the MiSEQ DNA sequencer (Illumina, San Diego, Calif.) were prepared using the HaloPlex V2 library preparation kit (Agilent, Santa Clara, Calif.). Sequencing was conducted using Courtagen Life Sciences, Inc.'s nucSEEK® and mtSEEK® Next Generation (NextGen®) sequencing panels. Sensitivity and specificity for detection of known variants exceeded 99% and 99.99% for the exonic sequence. Variants suspected to be related to disease, including those in TRAP1, were confirmed by Sanger sequencing.

For this study, a significant sequence variant was defined as evolutionarily conservation at least to Xenopus (frog) per the UCSC Genome Browser, with a single species allowed with a different sequence to account for potential sequence error in the database. Variant prevalence was compared to three different groups: 1: The general population (1000 Genomes); 2: Our referral population (95 unrelated patients without significant TRAP1 variants from our database, chosen to represent the larger 270 patients based on referring physician); and 3: a non-ATPase variant population (our unrelated cases with conserved TRAP1 variants in all gene regions outside of the ATPase domain). Since it was impractical to contact the physicians/families for additional information regarding the control patient groups, we used only the clinical information made available by the physician's office for all cases and controls. Statistical testing was performed by two-tailed Fisher exact test (available through graphpad.com/quickcalcs/contingency1/), without correction for multiple testing since this study did not result from data mining, but from follow-up of one variant seen in one patient. Odds ratios (OR) are given with 95% confidence interval (CI) without correction (available through vassarstats.net). Written informed consent was obtained from the adult patient and/or parent(s) for our case reports.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

What is claimed is:

1. A method of improving mitochondrial function in an individual at risk of or suffering from a mitochondrial dysfunction or disorder, the method comprising administering to the individual a therapeutically effective amount of an antioxidant, wherein DNA of the individual that encodes a TNF receptor-associated protein 1 (TRAP 1) gene product includes a change-of-function mutation, wherein said change-of-function mutation is a loss-of-function mutation.

2. The method of claim 1, wherein, prior to administration, the individual has been determined to possess the change-of-function mutation.

3. The method of claim 1, further comprising determining that the individual possesses the change-of-function mutation.

4. The method of claim 2, wherein the change-of-function mutation is in the ATPase domain or the C-terminal HSP90-like domain.

5. The method of claim 2, wherein the neurological and/or mitochondrial dysfunction or disorder is selected from the group consisting of functional gastrointestinal disorders, chronic pain disorders, chronic fatigue syndrome, intermittent encephalopathy, dementia and combinations thereof.

6. The method of claim 2, wherein the change-of-function mutation causes a changed ATPase activity of a TRAP 1 gene product, wherein the ATPase activity is reduced or increased.

7. The method of claim 2, wherein the change-of-function mutation is or comprises a mutation in the polypeptide of SEQ ID NO:1 selected from:

(i) the group consisting of 165Q>E, 192E>K, 216E>*, 253I>V, and combinations thereof, wherein * is a stop codon; or (ii) the group consisting of 266S>R, 340R>H, 388R>Q, 444Y>N, 445G>S, 457E>K, 469R>H, 535T>S, 685D>N, and combinations thereof.

8. The method of claim 2, wherein the change-of-function mutation is heterozygous.

9. The method of claim 2, wherein the change-of-function mutation is homozygous.

10. The method of claim 2, wherein the antioxidant is selected from the group consisting of Vitamin C, Vitamin A, Vitamin E, polyphenols, N-acetyl cysteine, Coenzyme Q10, alpha-tocopherol, alpha-tocotrienol, idebenone, cannabidiol, and pharmaceutically acceptable salts thereof.

11. The method of claim 3, wherein determining that the individual possesses the change-of-function mutation comprises requesting sequencing of at least a portion of nuclear DNA that encodes a TRAP 1 gene product.

12. The method of claim 3, wherein determining that the individual possesses the change-of-function mutation comprises sequencing at least a portion of nuclear DNA that encodes a TRAP 1 gene product.

13. The method of claim 3, wherein determining that the individual possesses the change-of-function mutation comprises requesting genotyping of at least a portion of nuclear DNA that encodes a TRAP 1 gene product.

14. The method of claim 3, wherein determining that the individual possesses the change-of-function mutation comprises genotyping at least a portion of nuclear DNA that encodes a TRAP 1 gene product.

15. The method of claim 1, wherein the individual is at risk of or suffers from a neurological dysfunction or disorder.

* * * * *